(12) United States Patent
Penning et al.

(10) Patent No.: US 8,183,250 B2
(45) Date of Patent: May 22, 2012

(54) POTENT PARP INHIBITORS

(75) Inventors: Thomas D. Penning, Elmhurst, IL (US);
Sheela A. Thomas, Libertyville, IL (US); Philip J. Hajduk, Mundelein, IL (US); Daryl R. Sauer, Trevor, WI (US); Kathy Sarris, Deerfield, IL (US); Vincent L. Giranda, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 282 days.

(21) Appl. No.: 12/476,849

(22) Filed: Jun. 2, 2009

(65) Prior Publication Data

US 2009/0298858 A1 Dec. 3, 2009

Related U.S. Application Data

(63) Continuation of application No. 11/765,776, filed on Jun. 20, 2007, now abandoned.

(60) Provisional application No. 60/805,235, filed on Jun. 20, 2006.

(51) Int. Cl.
*A01N 43/54* (2006.01)
*A61K 31/505* (2006.01)
*C07D 239/00* (2006.01)
*C07D 487/00* (2006.01)

(52) U.S. Cl. ........................ 514/267; 544/250
(58) Field of Classification Search ................ 514/267; 544/250
See application file for complete search history.

(56) References Cited

U.S. PATENT DOCUMENTS

| 4,105,764 | A | * | 8/1978 | Alexander | 514/233.2 |
| 4,105,766 | A | * | 8/1978 | Alexander | 514/267 |
| 4,105,966 | A | | 8/1978 | Lennon et al. | |
| 4,112,098 | A | | 9/1978 | Vogt | |
| 5,061,613 | A | * | 10/1991 | Kaneko | 430/558 |
| 2008/0146638 | A1 | | 6/2008 | Giranda et al. | |
| 2008/0280867 | A1 | | 11/2008 | Giranda et al. | |
| 2008/0293795 | A1 | | 11/2008 | Donawho et al. | |
| 2009/0029966 | A1 | | 1/2009 | Donawho et al. | |

FOREIGN PATENT DOCUMENTS

| EP | 374781 A2 | 6/1990 |
| EP | 394981 A2 | 10/1990 |
| JP | 03114891 | * 9/1989 |
| JP | 04037741 | * 6/1990 |
| JP | 3114891 A2 | 5/1991 |
| JP | 4037741 A2 | 2/1992 |
| JP | 4037941 A2 | 2/1992 |
| JP | 6222527 A2 | 8/1994 |
| JP | 20131811 A2 | 5/2000 |
| WO | WO-0050425 A1 | 8/2000 |
| WO | WO-0206284 A1 | 1/2002 |

OTHER PUBLICATIONS

Wright, Convenient Preparation of Pyrazolo[1,5-a]quinazolin-5(4H)-ones, J. of Heterocyclic Chemistry, 6(6), 947-8 (1969).*
Fleischer, et al., Synthesis of 2-[Mercapto(cyano)methylene]-1,2,3,4-tetrahydro-quinazolin-4-ones and 2-amino-4-methylpyrazolo-[1,5-a]quinazolin-5(4H)-one, J. Heterocyclic Chem., 34, 1251 (1997).*
Vasquez, et al., One-pot Microwave-assisted Preparation of Pyrazoloquinazolinone Libraries, Molecular Diversity, 7(2-4), 161-164 (2003).*
Lipunova, et al., Fluorine-containing Heterocycles: XII. Fluorine-containing Quinazolin-4-ones and Azolo[a]quinazolinone Derivatives, Russian Journal of Organic Chemistry, vol. 41, No. 7, 1071-1080 (2005).*
Peet, An Unexpected Aminolysis in the Synthesis of 5-substituted 3-(1H-tetrazol-5-yl)pyrazolo[1,5-a]quinazolines, J. of Heterocyclic Chemistry, 26(3), 713-16 (1989).*
Burkart, et al., "Mice lacking the poly(ADP-ribose) polymerase gene are resistant to pancreatic beta-cell destruction and diabetes development induced by streptozocin," Nature Medicine, 1999, 5—Issue 3, pp. 314-319.
Chen, et al., "Potentiation of the antitumor activity of cisplatin in mice by 3-aminobenzamide and nicotinamide," Cancer Chemotherapy and Pharmacology, 1998, 22, pp. 303-307.
Cuzzocrea, S., et al., "Protective effects of 3-aminobenzamide, an inhibitor of poly(ADP-ribose) synthase in a carrageenan-induced model of local inflammation," European Journal of Pharmacology, 1998, 342, pp. 67-76.
Ehrlich, W., et al., "Inhibition of the induction of collagenase by interleukin-1β in cultured rabbit synovial fibroblasts after treatment with the poly(ADP-ribose)-polymerase inhibitor 3-aminobenzamide," Rheumatol Int, 1995, 15, pp. 171-172.
International Search Report for application No. PCT/US2007/071649, Mailed on Oct. 12, 2007, 4 pages.
Kaneko et al., "Annelated pyrazolopyrimidin-5-one dyes for thermal-transfer recording," Chemical Abstracts Service, 1991.

(Continued)

*Primary Examiner* — Andrew D Kosar
*Assistant Examiner* — Erich A Leeser
(74) *Attorney, Agent, or Firm* — Susan L. Steele; Antonia Holland

(57) ABSTRACT

The present invention relates to 1H-benzimidazole-4-carboxamides of formula (I),

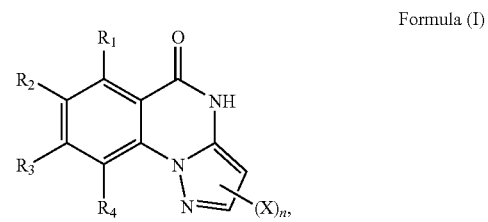

their preparation, and their use as inhibitors of the enzyme poly(ADP-ribose)polymerase for the preparation of drugs.

9 Claims, No Drawings

OTHER PUBLICATIONS

Kaneko et al., "Silver hanlide photographic material," Chemical Abstracts Service, 1992.

Kroger, H., et al., "Synergistic effects of thalidomide and poly(ADP-rose) polymerase inhibition on type Ii collagen-induced arthristis in mice ," Inflammation, 1996, 20—Issue 2, pp. 203-215.

Lipunova G. N. et al., "Fluorine-Containing Heterocycles: Part CII. Fluorine-Containing Ouinazolin-4-ones and Azolo[a]quinazolinone Derivatives," Russian Journal of Organic Chemistry, 2005, 41—Issue 7, pp. 1071-1080.

Michaelis et al., "1-Phenyl-5- and 3-pyrazolone-o-carboxylic Anhydrides," Chemical Abstracts Service, 373, pp. 129-212, 1910.

Peet Norton P., "An unexpected aminolysis in the synthesis of 5-substituted 3-(1H-tetrazol-5-yl)pyrazolo[1,5-a]quinazo lines," Journal of Heterocyclic Chemistry, 1989, 26—Issue 3, pp. 913-916.

Prescott, et al., "Lipid Vesicles as Carriers for Introducing Biologically Active Materials into Cells," Methods in Cell Biology, 1976, 33-71, vol. 14, Academic Press.

Supplementary European Search Report of EP Patent Application No. 7784490, dated Dec. 10, 2007, 5 pages total.

Szabo, C., et al., "Protection against peroxynitrite-induced fibroblast injury and arthritis development by inhibition of poly(ADP-ribose) synthase," Proc Natl Acad Sci USA, 1998, 95, pp. 3867-3872.

Thiemermann, C., et al., "Inhibition of the activity of poly (ADP ribose) synthetase reduces ischemia-reperfusion injury in the heart and skeletal muscle," Proc. Natal. Acad. Sci. USA, 1997, 94, pp. 679-683.

U.S. Appl. No. 11/970,828, filed Jan. 8, 2008, inventor Vincent L. Giranda.

U.S. Appl. No. 12/058,478, filed Mar. 28, 2008, inventor Vincent L. Giranda.

U.S. Appl. No. 12/116,823, filed May 7, 2008, inventor Cherrie K. Donawho.

U.S. Appl. No. 12/117,452, filed May 8, 2008, inventor Cherrie K. Donawho.

Vasquez TE et al., "One-pot microwave assisted preparation of pyrazoloouinazolinone libraries," Molecular Diversity, 2003, 7, pp. 161-164, ESCOM Science Publishers, Leiden, NFL.

Weltin, et al., "Immunosuppressive activities of 6(5h)-phenanthridinone, a new poly(adp-ribose)polymerase inhibitor," Int J Immunopharmac., 1995, 17—Issue4, pp. 265-271.

* cited by examiner

POTENT PARP INHIBITORS

This application is a continuation of U.S. application Ser. No. 11/765,776 filed on Jun. 20, 2007, which claims priority to U.S. Application No. 60/805,235 filed on Jun. 20, 2006, both of which are herein incorporated by reference.

TECHNICAL FIELD

The present invention relates to 1H-benzimidazole-4-carboxamides, their preparation, and their use as inhibitors of the enzyme poly(ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetominophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

SUMMARY OF THE INVENTION

In one embodiment, the present invention provides compounds of Formula (I)

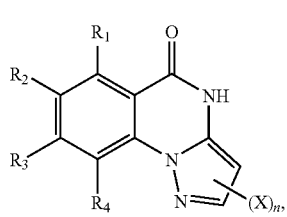

Formula (I)

or a pharmaceutically acceptable salt thereof, wherein
$R_1$, $R_2$, $R_3$ and $R_4$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

X is aryl, arylalkyl, alkyl, heteroaryl, heteroarylalkyl, heteroarylcarbonyl, heterocycle, heterocyclealkyl, heterocyclecarbonyl, hydroxyalkyl, cycloalkyl, cycloalkylalkyl, $NR_CR_D$, $(NR_CR_D)$carbonyl, $(NR_CR_D)$alkyl, $(NR_CR_D)$carbonylalkyl, or -alkyl-$CO_2G_1$;

wherein if X is aryl, arylalkyl, heteroaryl, heteroarylalkyl, heteroarylcarbonyl, heterocycle, heterocyclealkyl, heterocyclecarbonyl, cycloalkyl, or cycloalkylalkyl then X may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;

$G_1$ is hydrogen, alkyl, alkenyl, haloalkyl, aryl, arylalkyl, heteroaryl, heteroarylalkyl, cycloalkyl, cycloalkylalkyl, heterocycle, or heterocyclealkyl; wherein the aryl, the aryl moiety of arylalkyl, the heteroaryl, the heteroaryl moiety of heteroarylakyl, the cycloalkyl, the cycloalkyl moiety of cycloalkylalkyl, the heterocycle, and the heterocycle moiety of heterocyclealkyl are independently unsubstituted or substituted with 1, 2, 3, 4, or 5 substituents independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, carboxy, carboxyalkyl, hydroxy, hydroxyalkyl, $NR_AR_B$, $(NR_AR_B)$alkyl, $(NR_AR_B)$carbonyl, $(NR_AR_B)$carbonylalkyl, and oxo;

$R_C$ and $R_D$ are independently selected from the group consisting of hydrogen, alkyl, alkylcarbonyl, alkylcarbonyloxyalkylcarbonyl, arylcarbonyl, aryl, arylalkyl, arylalkylcarbonyl, carboxyalkyl, carboxyalkylcarbonyl, cycloalkyl, cycloalkylalkyl, haloalkyl, haloalkylcarbonyl, heteroaryl, heteroarylalkyl, heteroarylcarbonyl, heterocycle, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are aryl, arylalkyl, arylalkylcarbonyl, arylcarbonyl, cycloalkyl, cycloalkylalkyl, heteroaryl, heteroarylalkyl, heteroarylcarbonyl, heterocycle, heterocyclealkyl, heterocyclecarbonyl, or heterocyclealkylcarbonyl, then $R_C$ or $R_D$ may be unsubstituted or substituted with 1, 2, 3, 4, or 5 substituents independently selected from the group consisting of alkyl, alkenyl, alkynyl, nitro, —CN, halogen, haloalkyl, oxo, alkoxy, alkylcarbonyl, alkylcarbonylalkyl, alkoxyalkyl, alkoxycarbonyl, alkoxycarbonylalkyl, aryl, arylalkyl, arylalkoxy, arylalkylcarbonyl, and arylalkoxycarbonyl;

$R_A$ and $R_B$ are independently selected from the group consisting of hydrogen, alkyl, haloalkyl, and alkylcarbonyl; and
n is 1.

DETAILED DESCRIPTION OF THE INVENTION

In another embodiment, the present invention provides compounds of Formula (I)

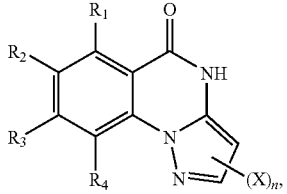

Formula (I)

or a pharmaceutically acceptable salt thereof, wherein $R_1$, $R_2$, $R_3$ and $R_4$ are hydrogen;

X is aryl, arylalkyl, alkyl, heteroaryl, heteroarylcarbonyl, heterocycle, heterocyclealkyl, heterocyclecarbonyl, hydroxyalkyl, cycloalkyl, $(NR_CR_D)$carbonyl, or $(NR_CR_D)$alkyl; wherein if X is aryl, arylalkyl, heteroaryl, heterocycle, heterocyclealkyl, heterocyclecarbonyl, or cycloalkyl, then X may be unsubstituted or substituted with 1 or 2 substituents, Z, independently selected from the group consisting of alkyl, nitro, —CN, halogen, alkoxy, alkoxycarbonyl, aryl, arylalkyl, arylalkoxycarbonyl, carboxy, cycloalkylalkyl, heteroaryl, heteroarylalkyl, heterocycle, heterocyclealkyl, heterocyclealkylcarbonyl, $NR_CR_D$, $(NR_CR_D)$alkyl, $(NR_CR_D)$carbonyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;

$R_C$ and $R_D$ are independently selected from the group consisting of hydrogen, alkyl, alkylcarbonyl, alkylcarbonyloxyalkylcarbonyl, aryl, arylalkyl, arylalkylcarbonyl, arylcarbonyl, carboxyalkyl, carboxyalkylcarbonyl, cycloalkyl, haloalkyl, haloalkylcarbonyl, heteroaryl, heteroarylcarbonyl, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are arylalkylcarbonyl, arylcarbonyl, heteroarylcarbonyl, heterocyclealkyl, heterocyclecarbonyl, or heterocyclealkylcarbonyl, then $R_C$ or $R_D$ may be unsubstituted or substituted with one substituent selected from the group consisting of alkoxy, alkylcarbonyl and arylalkoxycarbonyl;

$R_A$ and $R_B$ are independently selected from the group consisting of hydrogen, alkyl, and alkylcarbonyl; and n is 1.

In another embodiment the present invention provide compounds of Formula (I) where X is selected from the group consisting of aryl, heteroaryl, heterocycle, and cycloalkyl.

In another embodiment, the present invention provides compounds of Formula (II)

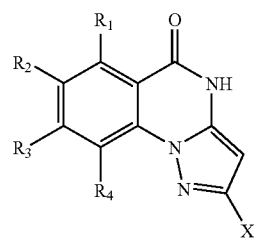

Formula (II)

or a therapeutically acceptable salt thereof, wherein $R_1$, $R_2$, $R_3$ and $R_4$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

X is aryl, arylalkyl, alkyl, heteroaryl, heteroarylalkyl, heteroarylcarbonyl, heterocycle, heterocyclealkyl, heterocyclecarbonyl, hydroxyalkyl, cycloalkyl, cycloalkylalkyl, $NR_CR_D$, $(NR_CR_D)$carbonyl, $(NR_CR_D)$alkyl, $(NR_CR_D)$carbonylalkyl, or -alkyl-$CO_2G_1$; wherein if X is aryl, arylalkyl, heteroaryl, heteroarylalkyl, heteroarylcarbonyl, heterocycle, heterocyclealkyl, heterocyclecarbonyl, cycloalkyl, or cycloalkylalkyl then X may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;

$G_1$ is hydrogen, alkyl, alkenyl, haloalkyl, aryl, arylalkyl, heteroaryl, heteroarylalkyl, cycloalkyl, cycloalkylalkyl, heterocycle, or heterocyclealkyl; wherein the aryl, the aryl moiety of arylalkyl, the heteroaryl, the heteroaryl moiety of heteroarylakyl, the cycloalkyl, the cycloalkyl moiety of cycloalkylalkyl, the heterocycle, and the heterocycle moiety of heterocyclealkyl are independently unsubstituted or substituted with 1, 2, 3, 4, or 5 substituents independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, carboxy, carboxyalkyl, hydroxy, hydroxyalkyl, $NR_AR_B$, $(NR_AR_B)$alkyl, $(NR_AR_B)$carbonyl, $(NR_AR_B)$carbonylalkyl, and oxo;

$R_C$ and $R_D$ are independently selected from the group consisting of hydrogen, alkyl, alkylcarbonyl, alkylcarbonyloxyalkylcarbonyl, aryl, arylalkyl, arylalkylcarbonyl, arylcarbonyl, carboxyalkyl, carboxyalkylcarbonyl, cycloalkyl, cycloalkylalkyl, haloalkyl, haloalkylcarbonyl, heteroaryl, heteroarylalkyl, heteroarylcarbonyl, heterocycle, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are aryl, arylalkyl, arylalkylcarbonyl, arylcarbonyl, cycloalkyl, cycloalkylalkyl, heteroaryl, heteroarylalkyl, heteroarylcarbonyl, heterocycle, heterocyclealkyl, heterocyclecarbonyl, or heterocyclealkylcarbonyl, then $R_C$ or $R_D$ may be unsubstituted or substituted with 1, 2, 3, 4, or 5 substituents independently selected from the group consisting of alkyl, alkenyl, alkynyl, nitro, —CN, halogen, haloalkyl, oxo, alkoxy, alkylcarbonyl, alkylcarbonylalkyl, alkoxyalkyl, alkoxycarbonyl, alkoxycarbonylalkyl, aryl, arylalkyl, arylalkoxy, arylalkylcarbonyl, and arylalkoxycarbonyl; and $R_A$ and $R_B$ are independently selected from the group consisting of hydrogen, alkyl, haloalkyl, and alkylcarbonyl.

In another embodiment, the present invention provides compounds of Formula (III)

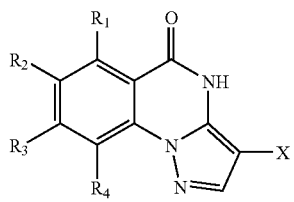

Formula (III)

or a pharmaceutically acceptable salt thereof, wherein $R_1$, $R_2$, $R_3$ and $R_4$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

X is aryl, arylalkyl, alkyl, heteroaryl, heteroarylalkyl, heteroarylcarbonyl, heterocycle, heterocyclealkyl, heterocyclecarbonyl, hydroxyalkyl, cycloalkyl, cycloalkylalkyl, $NR_CR_D$, $(NR_CR_D)$carbonyl, $(NR_CR_D)$alkyl, $(NR_CR_D)$carbonylalkyl, or -alkyl-$CO_2G_1$;

wherein if X is aryl, arylalkyl, heteroaryl, heteroarylalkyl, heteroarylcarbonyl, heterocycle, heterocyclealkyl, heterocyclecarbonyl, cycloalkyl, or cycloalkylalkyl then X may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;

$G_1$ is hydrogen, alkyl, alkenyl, haloalkyl, aryl, arylalkyl, heteroaryl, heteroarylalkyl, cycloalkyl, cycloalkylalkyl, heterocycle, or heterocyclealkyl; wherein the aryl, the aryl moiety of arylalkyl, the heteroaryl, the heteroaryl moiety of heteroarylalkyl, the cycloalkyl, the cycloalkyl moiety of cycloalkylalkyl, the heterocycle, and the heterocycle moiety of heterocyclealkyl are independently unsubstituted or substituted with 1, 2, 3, 4, or 5 substituents independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, carboxy, carboxyalkyl, hydroxy, hydroxyalkyl, $NR_AR_B$, $(NR_AR_B)$alkyl, $(NR_AR_B)$carbonyl, $(NR_AR_B)$carbonylalkyl, and oxo;

$R_C$ and $R_D$ are independently selected from the group consisting of hydrogen, alkyl, alkylcarbonyl, alkylcarbonyloxyalkyl, aryl, arylalkyl, arylalkylcarbonyl, carboxyalkyl, carboxyalkylcarbonyl, cycloalkyl, cycloalkylalkyl, haloalkyl, haloalkylcarbonyl, heteroaryl, heteroarylalkyl, heteroarylcarbonyl, heterocycle, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are aryl, arylalkyl, arylalkylcarbonyl, cycloalkyl, cycloalkylalkyl, heteroaryl, heteroarylalkyl, heteroarylcarbonyl, heterocycle, heterocyclealkyl, heterocyclecarbonyl, or heterocyclealkylcarbonyl, then $R_C$ or $R_D$ may be unsubstituted or substituted with 1, 2, 3, 4, or 5 substituents independently selected from the group consisting of alkyl, alkenyl, alkynyl, nitro, —CN, halogen, haloalkyl, oxo, alkoxy, alkylcarbonyl, alkylcarbonylalkyl, alkoxyalkyl, alkoxycarbonyl, alkoxycarbonylalkyl, aryl, arylalkyl, arylalkoxy, arylalkylcarbonyl, and arylalkoxycarbonyl; and $R_A$ and $R_B$ are independently selected from the group consisting of hydrogen, alkyl, haloalkyl, and alkylcarbonyl.

In another embodiment, the present invention provides compounds of Formula (II) wherein X is aryl or arylalkyl wherein the aryl or arylalkyl may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, and $(NR_CR_D)$carbonylalkyl; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl.

In another embodiment, the present invention provides compounds of Formula (II) wherein X is heteroaryl which may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, and $(NR_CR_D)$carbonylalkyl; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl.

In another embodiment, the present invention provides compounds of Formula (II) wherein X is heterocycle or heterocyclealkyl wherein the heterocycle or heterocyclealkyl may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl.

In another embodiment, the present invention provides compounds of Formula (III) wherein X is heteroarylcarbonyl, heterocyclealkyl, heterocyclecarbonyl, hydroxyalkyl, $(NR_CR_D)$carbonyl, $(NR_CR_D)$alkyl, or aryl wherein if X is heteroarylcarbonyl, heterocyclealkyl, heterocyclecarbonyl, or aryl, then X may be unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl.

In another embodiment, the present invention provides compounds of Formula (I) wherein $R_1$, $R_2$, $R_3$ and $R_4$ are hydrogen.

In another embodiment, the present invention provides compounds of Formula (II) wherein $R_1$, $R_2$, $R_3$ and $R_4$ are hydrogen.

In another embodiment, the present invention provides compounds of Formula (III) wherein $R_1$, $R_2$, $R_3$ and $R_4$ are hydrogen. In another embodiment, the present invention provides compounds selected from the group consisting of
3-phenyl-4H-pyrazolo[1,5-a]quinazolin-5-one;
3-(4-chloro-phenyl)-4H-pyrazolo[1,5-a]quinazolin-5-one;
2-phenyl-4H-pyrazolo[1,5-a]quinazolin-5-one;
2-tert-butyl-4H-pyrazolo[1,5-a]quinazolin-5-one;
2-furan-2-yl-4H-pyrazolo[1,5-a]quinazolin-5-one;
2-thiophen-2-yl-4H-pyrazolo[1,5-a]quinazolin-5-one;
2-(4-methoxyphenyl)-4H-pyrazolo[1,5-a]quinazolin-5-one;
2-(3-nitrophenyl)-4H-pyrazolo[1,5-a]quinazolin-5-one;
2-(3-chlorophenyl)-4H-pyrazolo[1,5-a]quinazolin-5-one;
2-biphenyl-2-yl-4H-pyrazolo[1,5-a]quinazolin-5-one;
2-biphenyl-4-yl-4H-pyrazolo[1,5-a]quinazolin-5-one;
2-(3-aminophenyl)-4H-pyrazolo[1,5-a]quinazolin-5-one;
2-(2-chlorophenyl)-4H-pyrazolo[1,5-a]quinazolin-5-one;
2-[3-(2-aminoethylamino)phenyl]-4H-pyrazolo[1,5-a]quinazolin-5-one;
N-{2-[3-(5-oxo-4,5-dihydropyrazolo[1,5-a]quinazolin-2-yl)phenylamino]ethyl}-acetamide;
N-[3-(5-oxo-4,5-dihydropyrazolo[1,5-a]quinazolin-2-yl)phenyl]acetamide;
benzyl 4-({acetyl[3-(5-oxo-4,5-dihydropyrazolo[1,5-a]quinazolin-2-yl)phenyl]amino}methyl)piperidine-1-carboxylate;
2-[3-(2-dimethylaminoethylamino)phenyl]-4H-pyrazolo[1,5-a]quinazolin-5-one;
2-piperidin-3-yl-4H-pyrazolo[1,5-a]quinazolin-5-one;
2-(1-methylpiperidin-3-yl)-4H-pyrazolo[1,5-a]quinazolin-5-one;
2-(1-ethylpiperidin-3-yl)-4H-pyrazolo[1,5-a]quinazolin-5-one;
2-(1-isobutylpiperidin-3-yl)-4H-pyrazolo[1,5-a]quinazolin-5-one;
2-(1-cyclopropylmethylpiperidin-3-yl)-4H-pyrazolo[1,5-a]quinazolin-5-one;
2-[1-(3-piperidin-1-ylpropionyl)piperidin-3-yl]-4H-pyrazolo[1,5-a]quinazolin-5-one;
2-(1-propylpiperidin-3-yl)-4H-pyrazolo[1,5-a]quinazolin-5-one;
2-(1-benzylpiperidin-3-yl)-4H-pyrazolo[1,5-a]quinazolin-5-one;
2-(1-cyclopentylmethylpiperidin-3-yl)-4H-pyrazolo[1,5-a]quinazolin-5-one;
2-(1-pyridin-4-ylmethylpiperidin-3-yl)-4H-pyrazolo[1,5-a]quinazolin-5-one;
2-(1-isopropylpiperidin-3-yl)-4H-pyrazolo[1,5-a]quinazolin-5-one;
methyl 4-(5-oxo-4,5-dihydropyrazolo[1,5-a]quinazolin-2-yl)benzoate;
2-(3-fluoro-4-morpholin-4-ylphenyl)-4H-pyrazolo[1,5-a]quinazolin-5-one;
2-cyclopropyl-4H-pyrazolo[1,5-a]quinazolin-5-one;
2-(1-benzylpiperidin-4-yl)-4H-pyrazolo[1,5-a]quinazolin-5-one;
N-[3-(5-oxo-4,5-dihydropyrazolo[1,5-a]quinazolin-2-yl)phenyl]-3-piperidin-1-ylpropionamide;
2-piperidin-4-yl-4H-pyrazolo[1,5-a]quinazolin-5-one;
2-(4-pyrrolidin-1-ylmethylphenyl)-4H-pyrazolo[1,5-a]quinazolin-5-one;
2-(1-methylpiperidin-4-yl)-4H-pyrazolo[1,5-a]quinazolin-5-one;
2-(1-ethylpiperidin-4-yl)-4H-pyrazolo[1,5-a]quinazolin-5-one;
2-(1-propylpiperidin-4-yl)-4H-pyrazolo[1,5-a]quinazolin-5-one;
2-(1-cyclopropylmethylpiperidin-4-yl)-4H-pyrazolo[1,5-a]quinazolin-5-one;
2-(1-isobutylpiperidin-4-yl)-4H-pyrazolo[1,5-a]quinazolin-5-one;
2-(1-isopropylpiperidin-4-yl)-4H-pyrazolo[1,5-a]quinazolin-5-one;
2-pyrrolidin-3-yl-4H-pyrazolo[1,5-a]quinazolin-5-one;
benzyl 3-(5-oxo-4,5-dihydropyrazolo[1,5-a]quinazolin-2-yl)pyrrolidine-1-carboxylate;
2-(1-methylpyrrolidin-3-yl)-4H-pyrazolo[1,5-a]quinazolin-5-one;
2-(1-ethylpyrrolidin-3-yl)-4H-pyrazolo[1,5-a]quinazolin-5-one;
2-(1-cyclopropylmethylpyrrolidin-3-yl)-4H-pyrazolo[1,5-a]quinazolin-5-one;
2-piperidin-2-yl-4H-pyrazolo[1,5-a]quinazolin-5-one;
2-(1-methylpiperidin-2-yl)-4H-pyrazolo[1,5-a]quinazolin-5-one;
(S)-2-acetylamino-4-methyl-N-(5-oxo-4,5-dihydropyrazolo[1,5-a]quinazolin-3-ylmethyl)pentanamide;

(R)-2-methoxy-N-(5-oxo-4,5-dihydropyrazolo[1,5-a]
   quinazolin-3-ylmethyl)-2-phenylacetamide;
N-(5-oxo-4,5-dihydropyrazolo[1,5-a]quinazolin-3-ylm-
   ethyl)isonicotinamide;
N-(5-oxo-4,5-dihydropyrazolo[1,5-a]quinazolin-3-ylm-
   ethyl)-3-piperidin-1-yl-propionamide;
N-(5-oxo-4,5-dihydropyrazolo[1,5-a]quinazolin-3-ylm-
   ethyl)-3-pyrrolidin-1-yl-propionamide;
2-morpholin-4-yl-N-(5-oxo-4,5-dihydropyrazolo[1,5-a]
   quinazolin-3-ylmethyl)acetamide;
3-morpholin-4-yl-N-(5-oxo-4,5-dihydropyrazolo[1,5-a]
   quinazolin-3-ylmethyl)-propionamide;
2-phenethyl-4H-pyrazolo[1,5-a]quinazolin-5-one;
2-benzyl-4H-pyrazolo[1,5-a]quinazolin-5-one;
2-piperidin-4-ylmethyl-4H-pyrazolo[1,5-a]quinazolin-5-
   one;
2-(1-methylpiperidin-4-ylmethyl)-4H-pyrazolo[1,5-a]
   quinazolin-5-one;
2-(3-bromobenzyl)pyrazolo[1,5-a]quinazolin-5(4H)-one;
3-[(5-oxo-4,5-dihydropyrazolo[1,5-a]quinazolin-2-yl)me-
   thyl]benzonitrile;
2-[3-(aminomethyl)benzyl]pyrazolo[1,5-a]quinazolin-5
   (4H)-one;
2-(3-pyridin-3-ylbenzyl)pyrazolo[1,5-a]quinazolin-5(4H)-
   one;
2-[3-(2-oxopyrrolidin-1-yl)benzyl]pyrazolo[1,5-a]quinazo-
   lin-5(4H)-one;
3'-[(5-oxo-4,5-dihydropyrazolo[1,5-a]quinazolin-2-yl)me-
   thyl]-1,1'-biphenyl-2-carbaldehyde;
2-[3-(2-fluoropyridin-4-yl)benzyl]pyrazolo[1,5-a]quinazo-
   lin-5(4H)-one;
methyl 3-[(5-oxo-4,5-dihydropyrazolo[1,5-a]quinazolin-2-
   yl)methyl]benzoate;
3-[(4-methylpiperazin-1-yl)carbonyl]pyrazolo[1,5-a]
   quinazolin-5(4H)-one;
3-(pyrrolidin-1-ylcarbonyl)pyrazolo[1,5-a]quinazolin-5
   (4H)-one;
N,N-dimethyl-5-oxo-4,5-dihydropyrazolo[1,5-a]quinazo-
   line-3-carboxamide;
3-(piperidin-1-ylcarbonyl)pyrazolo[1,5-a]quinazolin-5(4H)-
   one;
N-cyclopropyl-5-oxo-4,5-dihydropyrazolo[1,5-a]quinazo-
   line-3-carboxamide;
5-oxo-4,5-dihydropyrazolo[1,5-a]quinazoline-3-carboxam-
   ide;
N-methyl-5-oxo-4,5-dihydropyrazolo[1,5-a]quinazoline-3-
   carboxamide;
N-ethyl-5-oxo-4,5-dihydropyrazolo[1,5-a]quinazoline-3-
   carboxamide;
N-benzyl-5-oxo-4,5-dihydropyrazolo[1,5-a]quinazoline-3-
   carboxamide;
5-oxo-N-(2-phenylethyl)-4,5-dihydropyrazolo[1,5-a]
   quinazoline-3-carboxamide;
3-(azepan-1-ylcarbonyl)pyrazolo[1,5-a]quinazolin-5(4H)-
   one;
3-(morpholin-4-ylcarbonyl)pyrazolo[1,5-a]quinazolin-5
   (4H)-one;
3-(piperazin-1-ylcarbonyl)pyrazolo[1,5-a]quinazolin-5
   (4H)-one;
N-cyclohexyl-5-oxo-4,5-dihydropyrazolo[1,5-a]quinazo-
   line-3-carboxamide;
3-(1H-imidazol-1-ylcarbonyl)pyrazolo[1,5-a]quinazolin-5
   (4H)-one;
5-oxo-N-(piperidin-4-ylmethyl)-4,5-dihydropyrazolo[1,5-a]
   quinazoline-3-carboxamide;
3-{[3-(aminomethyl)piperidin-1-yl]carbonyl}pyrazolo[1,5-
   a]quinazolin-5(4H)-one;

5-oxo-N-phenyl-4,5-dihydropyrazolo[1,5-a]quinazoline-3-
   carboxamide;
4-{[(5-oxo-4,5-dihydropyrazolo[1,5-a]quinazolin-3-yl)car-
   bonyl]amino}butanoic acid;
3-[(5-oxo-4,5-dihydropyrazolo[1,5-a]quinazolin-2-yl)me-
   thyl]benzoic acid;
5-oxo-N-(2-piperidin-1-ylethyl)-4,5-dihydropyrazolo[1,5-a]
   quinazoline-3-carboxamide;
3-(Hydroxymethyl)pyrazolo[1,5-a]quinazolin -5-(4H)-one;
3-[(5-oxo-4,5-dihydropyrazolo[1,5-a]quinazolin-2-yl)me-
   thyl]benzamide;
3-(aminomethyl)pyrazolo[1,5-a]quinazolin-5(4H)-one;
N-[(5-oxo-4,5-dihydropyrazolo[1,5-a]quinazolin-3-yl)me-
   thyl]glycine;
4-chloro-N-[(5-oxo-4,5-dihydropyrazolo[1,5-a]quinazolin-
   3-yl)methyl]butanamide;
4-oxo-4-{[(5-oxo-4,5-dihydropyrazolo[1,5-a]quinazolin-3-
   yl)methyl]amino}butanoic acid;
1-acetyl-N-[(5-oxo-4,5-dihydropyrazolo[1,5-a]quinazolin-
   3-yl)methyl]piperidine-4-carboxamide;
2-oxo-2-{[(5-oxo-4,5-dihydropyrazolo[1,5-a]quinazolin-3-
   yl)methyl]amino}ethyl acetate;
3-(pyrrolidin-1-ylmethyl)pyrazolo[1,5-a]quinazolin-5(4H)-
   one;
1-[(5-oxo-4,5-dihydropyrazolo[1,5-a]quinazolin-3-yl)me-
   thyl]pyrrolidine-2,5-dione;
and
N-((5-Oxo-4,5-dihydropyrazolo[1,5-a]quinazolin-3-yl)me-
   thyl)acetamide; In another embodiment, the present inven-
   tion provides a pharmaceutical composition comprising a
   compound of Formula (I), or a pharmaceutically accept-
   able salt thereof, in combination with a therapeutically
   acceptable carrier.

In another embodiment, the present invention provides a method of inhibiting PARP in a mammal in recognized need of such treatment comprising administering to the mammal a therapeutically acceptable amount of a compound of Formula (I) or a pharmaceutically acceptable salt thereof.

In another embodiment, the present invention provides a method of treating cancer in a mammal in recognized need of such treatment comprising administering to the mammal a therapeutically acceptable amount of a compound of Formula (I) or a pharmaceutically acceptable salt thereof.

In another embodiment, the present invention provides a method for decreasing tumor volume in a mammal in recognized need of such treatment comprising administering to the mammal a therapeutically acceptable amount of a compound of Formula (I) or a pharmaceutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a pharmaceutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a pharmaceutically acceptable salt thereof.

In another embodiment, the present invention provides a method of potentiation of radiation therapy in a mammal in recognized need of such treatment comprising administering to the mammal a therapeutically acceptable amount of a compound of Formula (I) or a pharmaceutically acceptable salt thereof.

In another embodiment, the present invention provides a method of treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a pharmaceutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a pharmaceutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a pharmaceutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a pharmaceutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a pharmaceutically acceptable salt thereof.

In another embodiment, the present invention provides a method of treating hypoglycemia in a mammal in recognized need of such treatment comprising administering to the mammal a therapeutically acceptable amount of a compound of Formula (I) or a pharmaceutically acceptable salt thereof.

In another embodiment, the present invention provides a method of treating retroviral infection in a mammal in recognized need of such treatment comprising administering to the mammal a therapeutically acceptable amount of a compound of Formula (I) or a pharmaceutically acceptable salt thereof.

In another embodiment, the present invention provides a method of treating liver toxicity following acetaminophen overdose in a mammal in recognized need of such treatment comprising administering to the mammal a therapeutically acceptable amount of a compound of Formula (I) or a pharmaceutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a pharmaceutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for inhibiting the PARP enzyme in a mammal in recognized need of such treatment.

In another embodiment, the present invention provides a use of a compound of Formula (I), or a pharmaceutically acceptable salt thereof, to prepare a medicament for inhibiting tumor growth in a mammal in recognized need of such treatment.

In another embodiment, the present invention provides a use of a compound of Formula (I), or a pharmaceutically acceptable salt thereof, to prepare a medicament for treating cancer in a mammal in recognized need of such treatment.

In another embodiment, the present invention provides a use of a compound of Formula (I), or a pharmaceutically acceptable salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, the present invention provides a use of a compound of Formula (I), or a pharmaceutically acceptable salt thereof, to prepare a medicament for potentiation of cytotoxic cancer therapy in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for potentiation of radiation in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating hypoglycemia in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating retroviral infection in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating liver toxicity following acetaminophen overdose in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a pharmaceutically acceptable salt thereof.

In another embodiment, the present invention provides a use of a compound of Formula (I), or a pharmaceutically acceptable salt thereof, to prepare a medicament for treating skin damage secondary to sulfur mustards in a mammal in recognized need of such treatment comprising administering to the mammal a therapeutically acceptable amount of a compound of Formula (I) or a pharmaceutically acceptable salt thereof.

In another embodiment, the present invention provides pharmaceutical compositions comprising a compound of Formula (I) or a pharmaceutically acceptable salt thereof, in combination with a therapeutically acceptable carrier.

Definitions

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkyl" as used herein, means a saturated, straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through a alkyl group, as defined herein.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonyloxyalkyl" as used herein, means an alkylcarbonyloxy group, as defined herein, appended to the parent molecular moiety through an alkyl group, as defined herein.

The term "alkylcarbonyloxyalkylcarbonyl" as used herein, means an alkylcarbonyloxyalkyl group, as defined herein, appended to the parent molecular moiety through a carbonyl group.

The term "alkylenyl" as used herein, means a divalent group derived from a saturated, straight or branched chain hydrocarbon of from 1 to 6 carbon atoms. Representative examples include, but are not limited to, —$CH_2$—, —$CH(CH_3)$—, —$C(CH_3)_2$—, —$CH_2CH_2$—, —$CH_2CH_2CH_2CH_2CH_2$—, —$CH_2CH_2CH_2$—, —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "arylalkoxy" as used herein, means an aryl group, as defined herein, appended to the parent molecular moiety through an alkoxy group, as defined herein.

The term "arylalkoxycarbonyl" as used herein, means an arylalkoxy group, as defined herein, appended to the parent molecular moiety through a carbonyl group, as defined herein.

The term "arylalkylcarbonyl" as used herein, means an arylalkyl group, as defined herein, appended to the parent molecular moiety through a carbonyl group, as defined herein. The alkyl of arylalkylcarbonyl groups of the present invention may be substituted with an alkoxy substituent.

The term "arylcarbonyl" as used herein, means an aryl group, as defined herein, appended to the parent molecular moiety through a carbonyl group, as defined herein The term "carbonyl" as used herein, means a —C(O)— group.

The term "carboxy" as used herein, means a —CO$_2$H group.

The term "cyano" as used herein, means a —CN group.

The term "carboxyalkyl" as used herein, means a carboxy group, as defined herein, appended to the parent molecular moiety through an alkyl group, as defined herein.

The term "carboxyalkylcarbonyl" as used herein, means a carboxyalkyl group, as defined herein, appended to the parent molecular moiety through a carbonyl group, as defined herein.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The term "cycloalkylalkoxy" as used herein, means a cycloalkyl group, as defined herein, appended to the parent molecular moiety through an alkoxy group, as defined herein.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means a cycloalkyl group, as defined herein, appended to the parent molecular moiety through a carbonyl group, as defined herein.

The term "formyl" as used herein, means a —C(O)H group.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, 3-chloropropyl, chloromethyl, 2-fluoroethyl, trifluoromethyl, pentafluoroethyl, and 2-chloro-3-fluoropentyl.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkylcarbonyl" as used herein, means a haloalkyl group, as defined herein, appended to the parent molecular moiety through a carbonyl group, as defined herein.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinymethyl.

The term "heteroarylcarbonyl" as used herein, means a heteroaryl, as defined herein, appended to the parent molecular moiety through a carbonyl group, as defined herein.

The term "heteroarylcarbonylalkyl" as used herein, means a heteroarylcarbonyl, as defined herein, appended to the parent molecular moiety through an alkyl group, as defined herein.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocyclealkyl" as used herein, means a heterocycle, as defined herein, appended to the parent molecular moiety through an alkyl group, as defined herein.

The term "heterocyclealkylcarbonyl" as used herein, means a heterocyclealkyl, as defined herein, appended to the parent molecular moiety through a carbonyl group, as defined herein.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means a —NO$_2$ group.

The term "NR$_A$R$_B$" as used herein, means two groups, R$_A$ and R$_B$, which are appended to the parent molecular moiety through a nitrogen atom.

The term "(NR$_A$R$_B$)alkyl" as used herein, means a NR$_A$R$_B$ group, as defined herein, appended to the parent molecular moiety through an alkyl group.

The term "(NR$_A$R$_B$)carbonyl" as used herein, means a NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)carbonylalkyl" as used herein, means a (NR$_A$R$_B$)carbonyl group, as defined herein, appended to the parent molecular moiety through an alkyl group, as defined herein.

The term "(NR$_A$R$_B$)alkylcarbonyl" as used herein, means a (NR$_A$R$_B$)alkyl group, as defined herein, appended to the parent molecular moiety through a carbonyl group, as defined herein.

The term "NR$_C$R$_D$" as used herein, means two groups, R$_C$ and R$_D$, which are appended to the parent molecular moiety through a nitrogen atom.

The term "(NR$_C$R$_D$)alkyl" as used herein, means a NR$_C$R$_D$ group, as defined herein, appended to the parent molecular moiety through an alkyl group.

The term "(NR$_C$R$_D$)carbonyl" as used herein, means a NR$_C$R$_D$ group, as defined herein, appended to the parent molecular moiety through a carbonyl group, as defined herein. Representative examples of (NR$_C$R$_D$)carbonyl include, but are not limited to, aminocarbonyl, (methylamino)carbonyl, (dimethylamino)carbonyl, and (ethylmethylamino)carbonyl.

The term "(NR$_C$R$_D$)carbonylalkyl" as used herein, means a (NR$_C$R$_D$)carbonyl group, as defined herein, appended to the parent molecular moiety through an alkyl group, as defined herein.

The term "oxo" as used herein, means a =O moiety.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity

Inhibition of PARP

Nicotinamide[2,5',8-3H]adenine dinucleotide and strepavidin SPA beads were purchased from Amersham Biosciences (UK) Recombinant Human Poly(ADP-Ribose) Polymerase (PARP) purified from *E. coli* and 6-Biotin-17-NAD$^+$, were purchase from Trevigen, Gaithersburg, Md. NAD$^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissolved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM MgCl$_2$. PARP reactions contained 1.5 μM [$^3$H]-NAD$^+$ (1.6 uCi/mmol), 200 nM biotinylated histone H1, 200 nM slDNA, and 1 nM PARP enzyme. Auto reactions utilizing SPA bead-based detection were carried out in 1001 volumes in white 96 well plates. Reactions were initiated by adding 50 μl of 2×NAD$^+$ substrate mixture to 50 μl of 2× enzyme mixture containing PARP and DNA. These reactions were terminated by the addition of 150 μl of 1.5 mM benzamide (~1000-fold over its IC50). 170 μl of the stopped reaction mixtures were transferred to streptavidin Flash Plates, incubated for 1 hr, and counted using a TopCount microplate scintillation counter. The K$_i$ data was determined from inhibition curves at various substrate concentrations and are shown in Table 1 for compounds of the present invention

TABLE 1

| \multicolumn{8}{c}{Inhibition of PARP (nM)} |
|---|---|---|---|---|---|---|---|
| 44 | 69 | 846 | 364 | 520 | >9500 | 266 | 178 |
| 40 | 142 | 299 | 390 | 920 | 550 | 350 | 774 |
| 277 | 46 | 1700 | 256 | 831 | 211 | >9500 | 35 |
| 6400 | 419 | 327 | 1000 | 214 | 1337 | 413 | 271 |
| 53 | 668 | 621 | 920 | 321 | 775 | >9500 | >9500 |
| >9500 | >9500 | >9500 | >9500 | >9500 | 9390 | >9500 | >9500 |
| >9500 | >9500 | 7960 | >9500 | >9500 | >9500 | >9500 | >9500 |
| >9500 | 55 | 146 | 255 | 213 | 114 | 1230 | 92 |
| 86 | 1880 | 31 | 164 | | | | |

Cellular PARP Assay:

C41 cells were treated with a compound of the present invention for 30 minutes in 96 well plate. PARP was then activated by damaging DNA with 1 mM $H_2O_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$ for representative compounds of the present invention are provided in Table 2.

TABLE 2

| \multicolumn{4}{c}{Cellular Activity $EC_{50}$ (nM)} |
|---|---|---|---|
| 16 | 9.6 | 1.1 | >1000 |
| 24 | >1000 | 106 | |

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing cell death of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting the free base of a compound of the present invention with a suitable acid. Representative acids include, but are not limited to acetatic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of the present invention may be administered as a pharmaceutical composition containing a compound of the present invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: CDI for carbonyl diimidazole; DBU for 1,8-diazabicyclo[5.4.0]undec-7-ene; DME for 1,2-dimethoxyethane; DMF for N,N-dimethylformamide; DMSO for dimethylsulfoxide; $Et_2O$ for diethyl ether; EtOAc for ethyl acetate; EtOH for ethanol; HPLC for high pressure liquid chromatography; LDA for lithium diisopropylamide; MeOH for methanol; psi for pounds per square inch; rt for room temperature; TFA for trifluoroacetic acid; THF for tetrahydrofuran, and TMS for trimethylsilane.

Synthetic Methods

The compounds and processes of the present invention will be better understood in connection with the following synthetic schemes which together illustrate the methods by which the compounds of the invention may be prepared. The synthesis of compounds of formula (I) wherein the groups $R_1$, $R_2$, $R_3$, $R_4$, X, $R_A$ and $R_B$ are as set forth in the summary of the invention unless otherwise noted, is exemplified in Schemes 1-4.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the convention manner, e.g. by eliminating the solvent from the residue and further purified according to methodologies generally known in the art such as, but are not limited to, crystallization, distillation, extraction, trituration and chromatography. Unless otherwise described, the starting materials and reagents are either commercially available or may be prepared by one skilled in the art from commercially available materials using methods described in the chemical literature.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Routine experimentation, including appropriate manipulation of the reaction conditions, reagents used and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well know to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of formula (I) may be accomplished by methods analogous to those described in the following schemes and in specific examples.

Compounds of formula (I) wherein X is represented by R' and R" and one of R' and R" is hydrogen, can be prepared using the general procedure as illustrated in scheme 1.

Scheme 1

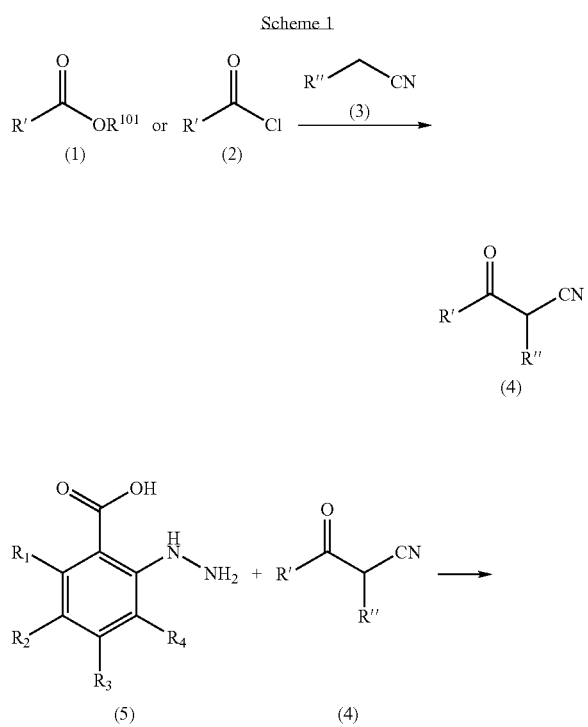

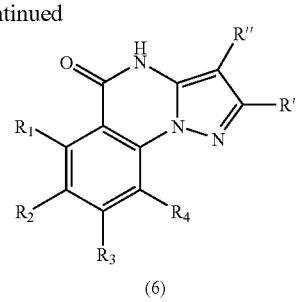

Compound of formula (6) can be obtained by (a) deprotonation of nitrile (3) with a base such as, but not limited to, n-butyl lithium and the (b) contacting the anion obtained from step (a) with an acid chloride (2) or an ester (1) wherein $R^{101}$ is $C_{1-6}$ alkyl, to provide compound (4). Alternatively, the anion obtained from step (a) can be treated with (1) wherein $R^{101}$ is hydrogen, in the presence of a coupling reagent such as, but not limited to, N,N'-carbonyldiimidazole or 1,3-dicyclohexylcarbodiimide, to provide compound (4). Treatment of 2-hydrazinobenzoic acid (5) and compound (4) in a acetic acid, in a microwave reactor and at elevated temperature (for example, 150° C.) generates 4H-pyrazolo[1,5-a]quinazolin-5-one (6) wherein one of R' and R" is hydrogen and the other is X (as defined in formula (I)).

Compounds having general formula (I) wherein X is $NR_CR_D$alkyl, $R_C$ is hydrogen or alkyl, and $R_D$ is alkyl, alkylcarbonyl, heteroarylcarbonyl, heterocyclealkylcarbonyl or $NR_AR_B$alkylcarbonyl, can be prepared as shown in Scheme 2.

Scheme 2

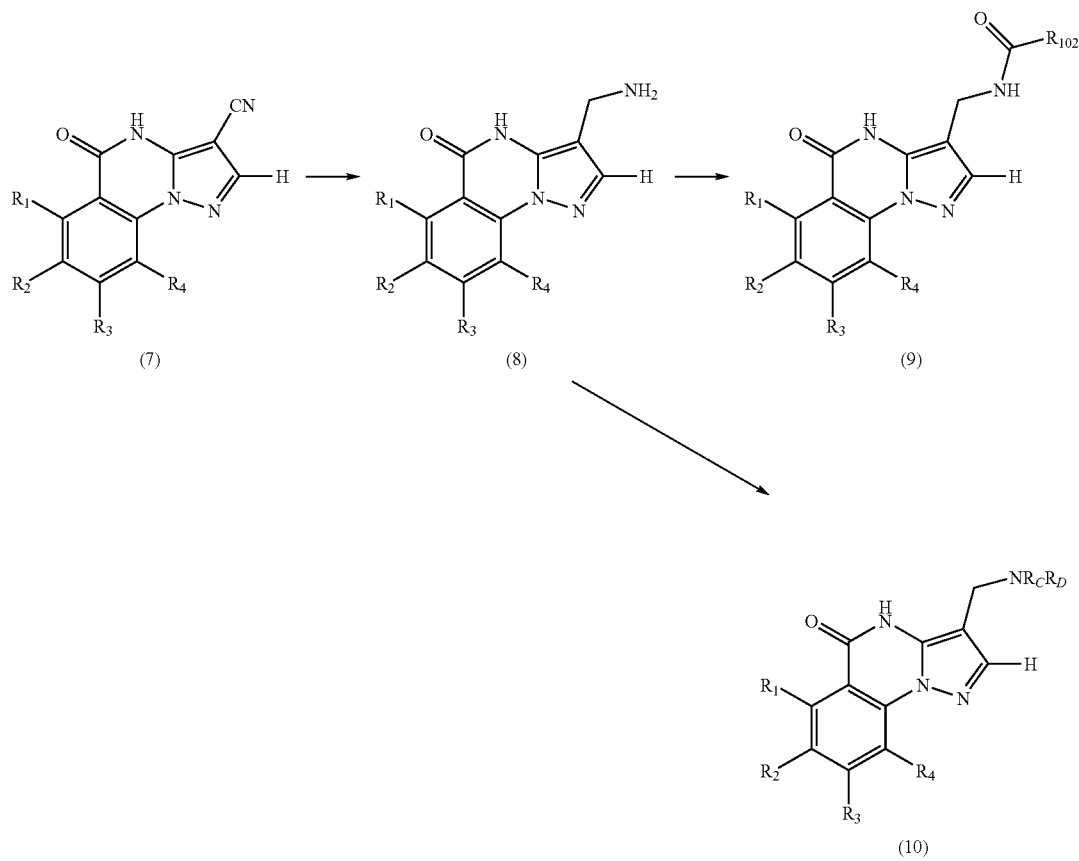

A 3-cyano-4H-pyrazolo[1,5-a]quinazolin-5-one (7), prepared using the conditions as described in Scheme 1, or purchased, can be reduced to the 3-aminomethyl analog (8) using an appropriate reducing agent such as ammonia in methanol and Raney nickel, under about 60 psi of hydrogen gas. Coupling of (8) with a carboxylic acid of formula $R_{102}COOH$ wherein $R_{102}$ is alkyl, heteroaryl, heterocyclealkyl or $NR_AR_B$alkyl, in the presence of a coupling reagent such as, but not limited to, 1,3-dicyclohexylcarbodiimide, a coupling auxiliary such as, but not limited to, 1-hydroxybenzotriazole hydrate, and a base such as, but not limited to diisopropylethyl amine, provides compound of formula (9). The reaction is generally performed in a solvent such as, but not limited to, N,N-dimethylacetamide, at ambient temperature or with heating (for example, at about 100-150° C.) and optionally in a microwave reactor. Compound (8) can also be coupled with an acid chloride $R_{102}COCl$ in the presence of a base such as pyridine and in a solvent such as DMF, or alternatively, (8) can be coupled with an anhydride $(R_{102}CO)_2O$ in the presence of a base such as diisopropylethylamine and in a solvent such as methanol. Compound (8) can also be alkylated with an halide of formula $R_{103}X$ wherein $R_{103}$ is alkyl, aralkyl, heteroarylalkyl, heterocyclealkyl or $NR_AR_B$alkyl, in the presence of a base such as sodium ethoxide or can be reacted with an aldehyde $R_{104}$—CHO or ketone $R_{104}R_{105}C(O)$ wherein $R_{104}$ and $R_{105}$ are alkyl, aryl, aralkyl, heteroaryl, heteroarylalkyl, heterocyclealkyl or $NR_AR_B$alkyl, under reductive amination conditions, such as sodium cyanoborohydride in methanol, to give the N-alkyl analog (10).

Compounds having general formula (I) wherein X is aryl, heteroaryl, heteroarylalkyl, or aralkyl, can be prepared as shown in Scheme 3.

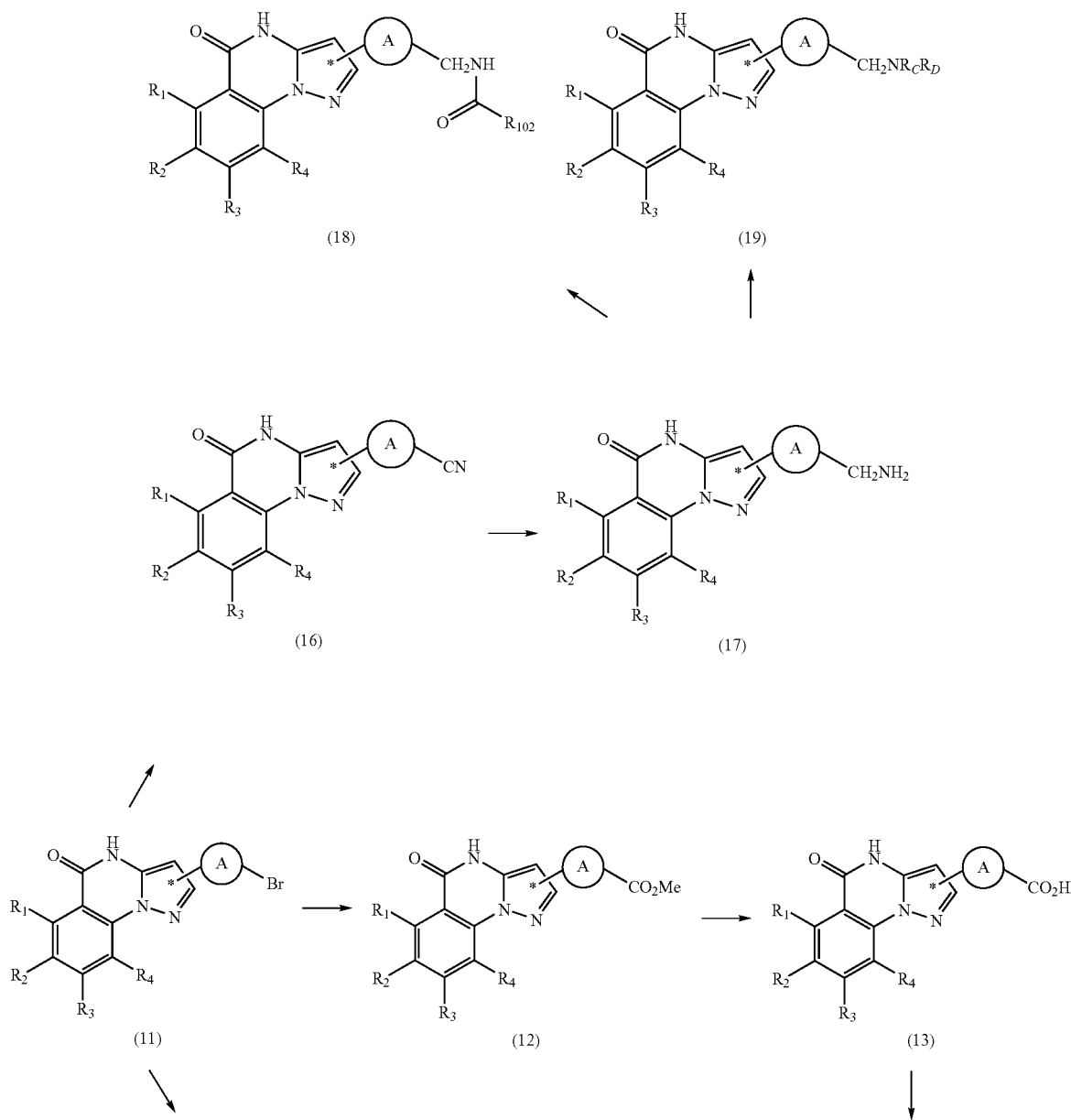

Scheme 3

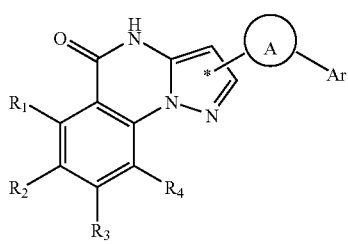

(15)

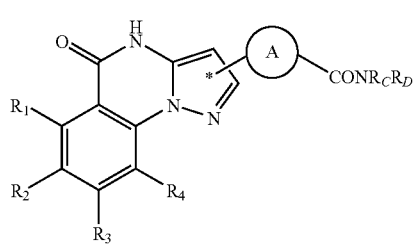

(14)

A bromo 2- or 3-aryl, heteroaryl, heteroarylalkyl, or aralkyl-4H-pyrazolo[1,5-a]quinazolin-5-one of formula (II), where A is aryl, heteroaryl, heteroarylalkyl, is prepared using the conditions as described in Scheme 1. This compound can be carbonylated under palladium catalysis in the presence of methanol or other alcohols to give the methyl ester (12). Saponification using, for example, sodium hydroxide in ethanol, gave the acid (13). Acid (13) can be converted to amide (14) using an amine $NHR_CR_D$ under standard peptide coupling conditions such as 1,3-dicyclohexylcarbodiimide or 1,1'-carbonyldiimidazole. Bromide (11) can also be coupled with an aryl or heteroaryl boronic acid or an aryl or heteroaryl trialkylstannane under palladium catalysis conditions to provide compounds of formula (15), where Ar is aryl or heteroaryl. In addition, bromide (11) can be converted to nitrile (16) using zinc cyanide under palladium catalysis conditions. Nitrile (16) can be reduced to amine (17) using, for example, Raney nickel and hydrogen. Amines of formula (17) can be further functionalized to amides (18) wherein $R_{102}$ is alkyl, arylalkyl, heterocycle, heterocyclealkyl, or $NR_AR_B$alkyl, and substituted amines (19) as described for the preparation of (9) and (10) in Scheme 2.

Compounds having general formula (I) wherein X is $NR_CR_D$carbonyl, $R_C$ and $R_D$ are hydrogen, alkyl, aryl, heteroaryl, heterocycle, heterocyclealkyl or $(NR_AR_B)$alkyl, can be prepared as shown in Scheme 4.

Scheme 4

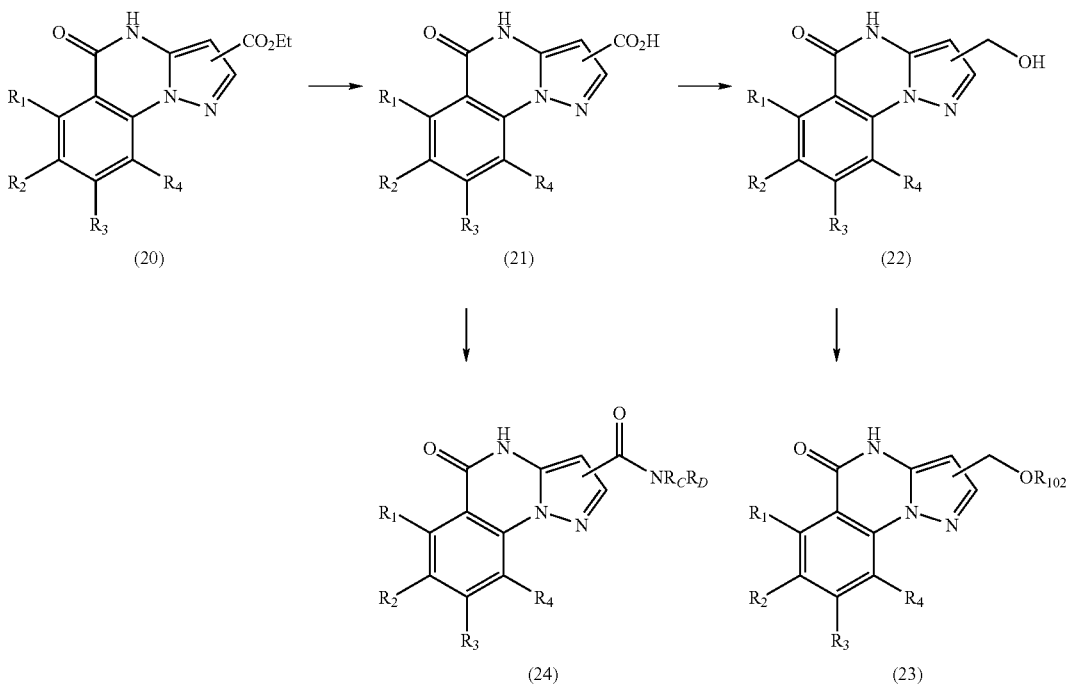

A 2- or 3-carboalkoxy-4H-pyrazolo[1,5-a]quinazolin-5-one (20), is prepared using the conditions as described in Scheme 1. This compound can be saponified to the corresponding carboxylic acid (21) under standard acidic (ie, hydrochloric acid) or basic (ie, sodium hydroxide) conditions. Reduction using a reducing agent such as lithium aluminum hydride in tetrahydrofuran provided the alcohol (22). This can be converted to ether (23) wherein $R_{102}$ is alkyl, heteroaryl, heterocyclealkyl or $(NR_AR_B)$alkyl, under standard Williamson ether synthesis conditions with an alkyl halide or under standard Mitsunobu conditions. Alternately, acid (21) can be converted to amide (24) using an amine $NHR_CR_D$ under standard peptide coupling conditions such as 1,3-dicyclohexylcarbodiimide or 1,1'-carbonyldiimidazole.

The following Examples are intended as an illustration of and not a limitation upon the scope of the invention as defined in the appended claims. The compounds of this invention can be prepared by a variety of synthetic routes.

EXAMPLE 1

3-phenyl-4H-pyrazolo[1,5-a]quinazolin-5-one

A mixture of 2-hydrazinobenzoic acid (0.15 g, 0.8 mmol) and 3-oxo-2-phenyl-propionitrile (0.116 g, 0.8 mmol) in acetic acid (0.2 mL) was heated in a microwave (Personal Chemistry SmithSynthesizer) at 150° C. for 10 minutes. The precipitated product was filtered, washed with methanol and diethyl ether and dried. $^1$H NMR (DMSO-$d_6$) δ 12.10 (s, 1H), 8.10-8.19 (m, 3H) 7.88-7.96 (m, 1H), 7.59 (d, J=7.3 Hz, 2H), 7.52 (t, J=7.8 Hz, 1H), 7.42 (t, J=7.6 Hz, 2 Hz), 7.28 (t, J=7.3 Hz, 1H).

EXAMPLE 2

3-(4-chloro-phenyl)-4H-pyrazolo[1,5-a]quinazolin-5-one

The title compound was prepared as described in EXAMPLE 1, substituting 2-(4-chlorophenyl)-3-oxo-propionitrile for 3-oxo-2-phenylpropionitrile. $^1$H NMR (DMSO-$d_6$) δ 12.14 (s, 1H), 8.12-8.19 (m, 2H) 7.89-7.94 (m, 1H), 7.62 (d, J=7.7 Hz, 2H), 7.53 (t, J=7.5 Hz, 1H), 7.44-7.48 (m, 2H).

EXAMPLE 3

2-phenyl-4H-pyrazolo[1,5-a]quinazolin-5-one

The title compound was prepared as described in EXAMPLE 1, substituting 3-oxo-3-phenylpropionitrile for 3-oxo-2-phenylpropionitrile. $^1$H NMR (DMSO-$d_6$) δ 12.30 (s, 1H), 8.15-8.18 (m, 2H) 7.97 (d, J=7.1 Hz, 2H), 7.91 (t, J=7.8 Hz, 1H), 7.45-7.53 (m, 3H), 7.40 (t, J=7.2 Hz, 1H), 6.38 (s, 1H).

EXAMPLE 4

2-tert-butyl-4H-pyrazolo[1,5-a]quinazolin-5-one

The title compound was prepared as described in EXAMPLE 1, substituting 4,4-dimethyl-3-oxo-pentanenitrile for 3-oxo-2-phenylpropionitrile. $^1$H NMR (DMSO-$d_6$) δ 12.09 (s, 1H), 8.11 (dd, J=8.0, 1.2 Hz, 1H) 8.02 (d, J=7.7 Hz, 2H), 7.82-7.87 (m, 1H), 7.41-7.46 (m, 1H), 5.80 (s, 1H), 1.32 (s, 9H).

EXAMPLE 5

2-furan-2-yl-4H-pyrazolo[1,5-a]quinazolin-5-one

The title compound was prepared as described in EXAMPLE 1, substituting 3-furan-2-yl-3-oxopropionitrile for 3-oxo-2-phenylpropionitrile. $^1$H NMR (DMSO-$d_6$) δ 12.28 (s, 1H), 8.08-8.17 (m, 2H), 7.90 (td, J=7.8, 1.5 Hz, 1H), 7.80 (d, J=1.8 Hz, 1H), 7.50 (t, J=7.7 Hz, 1H), 6.99 (d, J=3.4 Hz, 1H), 6.64 (dd, J=3.4, 1.8 Hz, 1H), 6.19 (s, 1H).

EXAMPLE 6

2-thiophen-2-yl-4H-pyrazolo[1,5-a]quinazolin-5-one

The title compound was prepared as described in EXAMPLE 1, substituting 3-oxo-3-thiophen-2-yl-propionitrile for 3-oxo-2-phenylpropionitrile. $^1$H NMR (DMSO-$d_6$) δ 12.30 (s, 1H), 8.15 (d, J=8.0 Hz, 1H) 8.08 (d, J=7.7 Hz, 1H), 7.90 (td, J=7.8, 1.5 Hz, 1H), 7.58-7.65 (m, 2H), 7.47-7.53 (m, 1H), 7.15 (dd, J=5.1, 3.5 Hz, 1H), 6.30 (s, 1H).

EXAMPLE 7

2-(4-methoxyphenyl)-4H-pyrazolo[1,5-a]quinazolin-5-one

The title compound was prepared as described in EXAMPLE 1, substituting 3-(4-methoxyphenyl)-3-oxo-propionitrile for 3-oxo-2-phenylpropionitrile. $^1$H NMR (DMSO-$d_6$) δ 12.25 (s, 1H), 8.12-8.17 (m, 2H), 7.87-7.92 (m, 3H), 7.46-7.51 (m, 1H), 7.03 (d, J=8.9, Hz, 2H), 6.30 (s, 1H), 3.82 (s, 3H).

EXAMPLE 8

2-(3-nitrophenyl)-4H-pyrazolo[1,5-a]quinazolin-5-one

The title compound was prepared as described in EXAMPLE 1, substituting 3-(3-nitrophenyl)-3-oxo-propionitrile for 3-oxo-2-phenylpropionitrile. $^1$H NMR (DMSO-$d_6$) δ 12.40 (s, 1H), 8.74-8.76 (m, 1H), 8.42 (dd, J=6.4, 1.5 Hz, 1H), 8.16-8.26 (m, 3H), 7.90-7.95 (m, 1H), 7.78 (t, J=8.0 Hz, 1H), 7.52-7.56 (m, 1H), 6.59 (s, 1H).

EXAMPLE 9

2-(3-chlorophenyl)-4H-pyrazolo[1,5-a]quinazolin-5-one

The title compound was prepared as described in EXAMPLE 1, substituting 3-(3-chlorophenyl)-3-oxo-propionitrile for 3-oxo-2-phenylpropionitrile. $^1$H NMR (DMSO-$d_6$) δ 12.37 (s, 1H), 8.19 (d, J=7.9 Hz, 1H), 8.16 (dd, J=7.9, 1.2 Hz, 1H), 8.04 (t, J=1.8 Hz, 1H), 7.95 (d, J=7.6 Hz, 1H), 7.87-7.94 (m, 1H), 7.45-7.54 (m, 3H), 6.49 (s, 1H).

EXAMPLE 10

2-biphenyl-2-yl-4H-pyrazolo[1,5-a]quinazolin-5-one

The title compound was prepared as described in EXAMPLE 1, substituting 3-biphenyl-2-yl-3-oxo-propionitrile for 3-oxo-2-phenylpropionitrile. $^1$H NMR (DMSO-$d_6$) δ 11.94 (s, 1H), 8.11 (dd, J=7.9, 1.2 Hz, 1H), 8.05 (d, J=8.2 Hz, 1H), 7.85-7.92 (m, 2H), 7.46-7.53 (m, 3H), 7.33-7.41 (m, 4H), 7.28 (dd, J=7.8, 1.7 Hz, 2H), 5.19 (s, 1H).

EXAMPLE 11

2-biphenyl-4-yl-4H-pyrazolo[1,5-a]quinazolin-5-one

The title compound was prepared as described in EXAMPLE 1, substituting 3-biphenyl-4-yl-3-oxo-propionitrile for 3-oxo-2-phenylpropionitrile. $^1$H NMR (DMSO-$d_6$) δ 12.29 (s, 1H), 8.14-8.20 (m, 2H), 7.92 (td, J=7.3, 2.1 Hz, 2H), 7.57-7.63 (m, 1H), 7.53 (t, J=7.0 Hz, 1H), 7.44-7.50 (m, 2H), 6.39 (s, 1H).

EXAMPLE 12

2-(3-aminophenyl)-4H-pyrazolo[1,5-a]quinazolin-5-one

A mixture of EXAMPLE 8 (1.07 g, 3.5 mmol) and 10% palladium on carbon (0.2 g) in methanol (25 mL) was stirred overnight under 1 atmosphere of hydrogen and filtered. The filtrate was concentrated and the residue crystallized from methanol to provide the title compound (0.58 g, 60%). $^1$H NMR (DMSO-d$_6$) δ 12.23 (s, 1H), 8.10-8.18 (m, 2H), 7.86-7.95 (m, 1H), 7.49 (t, J=7.0 Hz, 1H), 7.19 (s, 1H), 7.05-7.12 (m, 2H), 6.56-6.63 (m, 1H), 6.20 (s, 1H), 5.19 (s, 2H).

EXAMPLE 13

2-(2-chlorophenyl)-4H-pyrazolo[1,5-a]quinazolin-5-one

The title compound was prepared as described in EXAMPLE 1, substituting 3-(2-chlorophenyl)-3-oxo-propionitrile for 3-oxo-2-phenylpropionitrile. $^1$H NMR (DMSO-d$_6$) δ 12.34 (s, 1H), 8.15-8.21 (m, 2H), 8.07 (d, J=8.2 Hz, 2H), 7.90-7.95 (m, 1H), 7.73-7.81 (m, 4H), 7.51 (q, J=7.7 Hz, 3H), 7.40 (t, J=7.3 Hz, 1H), 6.44 (s, 1H).

EXAMPLE 14

2-[3-(2-aminoethylamino)phenyl]-4H-pyrazolo[1,5-a]quinazolin-5-one

A solution of EXAMPLE 12 (0.06 g, 0.2 mmol) and tert-butyl (2-oxoethyl)carbamate (0.035 g, 0.2 mmol) in ethanol (1 mL) and acetonitrile (1 mL) was treated with sodium cyanoborohydride (0.014 g, 0.2 mmol) and acetic acid (0.2 mL). The mixture was heated in a microwave at 170° C. for 40 minutes and concentrated. The residue was purified by flash chromatography on silica gel with 10% methanol/dichloromethane/0.1% ammonium hydroxide to provide the title compound. $^1$H NMR (DMSO-d$_6$) δ 12.30 (s, 1H), 10.06 (s, 1H), 8.11-8.19 (m, 2H), 7.89-7.96 (m, 1H), 7.58-7.67 (m, 2H), 7.52 (t, J=7.6 Hz, 1H), 7.39 (t, J=7.9 Hz, 1H), 6.27 (s, 1H), 3.30-3.36 (m, 4H), 2.08 (s, 3H).

EXAMPLE 15

N-{2-[3-(5-oxo-4,5-dihydropyrazolo[1,5-a]quinazolin-2-yl)phenylamino]ethyl}-acetamide The title compound was obtained as a byproduct in the purification of EXAMPLE 14. $^1$H NMR (DMSO-d$_6$) δ 12.25 (s, 1H), 8.12-8.18 (m, 2H), 7.91 (td, J=7.8, 1.5 Hz, 2H), 7.47-7.53 (m, 1H), 7.13-7.20 (m, 2H), 6.60-6.68 (m, 1H), 6.27 (s, 1H), 3.22-3.26 (m, 2H), 3.14-3.19 (m, 2H), 1.76 (s, 3H).

EXAMPLE 16

N-[3-(5-oxo-4,5-dihydropyrazolo[1,5-a]quinazolin-2-yl)phenyl]acetamide

A solution of EXAMPLE 12 (0.04 g, 0.1 mmol) and acetic anhydride (0.02 mL, 1.5 mmol) in acetonitrile was treated with triethylamine (0.1 mL, 0.8 mmol). The mixture was stirred overnight at ambient temperature and filtered to provide the title compound. $^1$H NMR (DMSO-d$_6$) δ 12.27 (s, 1H), 10.04 (s, 1H), 8.11-8.20 (m, 3H), 7.87-7.95 (m, 1H), 7.58-7.66 (m, 2H), 7.48-7.56 (m, 1H), 7.38 (t, J=7.8 Hz, 1H), 6.27 (s, 1H), 2.06-2.12 (m, 3H).

EXAMPLE 17

Benzyl 4-({acetyl[3-(5-oxo-4,5-dihydropyrazolo[1,5-a]quinazolin-2-yl)phenyl]amino}methyl)piperidine-1-carboxylate The title compound was prepared as described in EXAMPLE 14, substituting benzyl 4-formylpiperidine-1-carbamate for tert-butyl (2-oxoethyl)carbamate. $^1$H NMR (DMSO-d$_6$) δ 8.15-8.20 (m, 2H), 7.88-7.98 (m, 3H), 7.49-7.57 (m, 2H), 7.30-7.38 (m, 6H), 6.49 (s, 1H), 5.05 (s, 2H), 3.94 (s, 2H), 3.64 (d, J=6.8 Hz, 2H), 3.37-3.42 (m, 1H), 3.35 (s, 3H), 1.77-1.84 (m, 2H), 1.68 (d, J=12.0 Hz, 3H), 1.09 (t, J=6.9 Hz, 2H).

EXAMPLE 18

2-[3-(2-dimethylaminoethylamino)phenyl]-4H-pyrazolo[1,5-a]quinazolin-5-one

A solution of EXAMPLE 12 (0.04 g, 0.1 mmol) and (2-bromoethyl) dimethylamine (0.02 g, 0.1 mmol) in acetonitrile (1 mL) was treated with potassium carbonate (0.04 g, 0.3 mmol). The mixture was stirred overnight at 50° C. and filtered. The filtrate was concentrated and purified by flash chromatography on silica gel with 10% methanol/dichloromethane to provide the title compound. $^1$H NMR (DMSO-d$_6$) δ 8.12-8.18 (m, 2H), 7.86-7.95 (m, 1H), 7.49 (t, J=7.6 Hz, 1H), 7.12-7.20 (m, 3H), 6.64 (s, 1H), 6.27 (s, 1H), 3.23-3.26 (m, 3H), 2.57-2.65 (m, 1H), 2.31 (s, 6H), 1.24 (s, 1H), 0.85 (s, 1H).

EXAMPLE 19

2-piperidin-3-yl-4H-pyrazolo[1,5-a]quinazolin-5-one

The title compound was prepared as described in EXAMPLE 1, substituting tert butyl 3-(2-cyanoacetyl)piperidine-1-carboxylate for 3-oxo-2-phenylpropionitrile. $^1$H NMR (DMSO-d$_6$) δ 12.23 (s, 1H), 8.85 (s, 2H), 8.13 (d, J=8.0 Hz, 1H), 8.04 (d, J=7.7 Hz, 1H), 7.88 (td, J=7.8, 1.53 Hz, 1H), 7.46-7.51 (m, 1H), 5.91 (s, 1H), 3.44-3.52 (m, 1H), 3.27-3.33 (m, 2H), 3.09-3.21 (m, 2H), 2.92 (s, 1H), 2.04-2.11 (m, 1H), 1.84-1.91 (m, 1H), 1.71-1.82 (m, 1H).

EXAMPLE 20

2-(1-methylpiperidin-3-yl)-4H-pyrazolo[1,5-a]quinazolin-5-one

A solution of EXAMPLE 19 (0.04 g, 0.1 mmol) and formaldehyde (36% in water, 0.018 mL, 2 mmol) in methanol (1 mL) was treated with sodium cyanoborohydride (0.009 g, 0.1 mmol) and acetic acid (0.1 mL). The mixture was stirred overnight at ambient temperature and concentrated. The residue was purified by HPLC on a C18 column with 0-100% acetonitrile/water/0.1% trifluoroacetic acid to provide the title compound as the trifluoroacetate salt. $^1$H NMR (CD$_3$OD) δ 8.23 (d, J=7.1 Hz, 1H), 8.15 (d, J=8.0 Hz, 1H), 7.84-7.89 (m, 1H), 7.46-7.52 (m, 1H), 5.95 (s, 1H), 3.63-3.74 (m, 1H), 3.35-3.48 (m, 3H), 3.05-3.17 (m, 1H), 2.94 (s, 3H), 2.15-2.24 (m, 1H), 2.01-2.08 (m, 1H), 1.84-1.95 (m, 2H).

EXAMPLE 21

2-(1-ethylpiperidin-3-yl)-4H-pyrazolo[1,5-a]quinazolin-5-one

The title compound was prepared as the trifluoroacetate salt as described in EXAMPLE 20, substituting acetaldehyde for formaldehyde. $^1$H NMR (CD$_3$OD) δ 8.23 (dd, J=8.0, 1.5 Hz, 1H), 8.14 (d, J=8.0 Hz, 1H), 7.87 (td, J=7.8, 1.2 Hz, 1H), 7.47-7.51 (m, 1H), 5.96 (s, 1H), 3.65 (s, 1H), 3.49 (d, J=7.1 Hz, 1H), 3.19 (dd, J=7.2, 2.3 Hz, 3H), 3.01 (s, 1H), 2.19 (s, 1H), 2.03 (s, 1H), 1.85-1.97 (m, 2H), 1.40 (t, J=7.4 Hz, 3H).

EXAMPLE 22

2-(1-isobutylpiperidin-3-yl)-4H-pyrazolo[1,5-a]quinazolin-5-one

The title compound was prepared as the trifluoroacetate salt as described in EXAMPLE 20, substituting 2-methylpropionaldehyde for formaldehyde. $^1$H NMR (DMSO-d$_6$) δ 12.26 (s, 1H), 8.12-8.19 (m, 1H), 8.02 (d, J=7.6 Hz, 1H), 7.86-7.92 (m, 1H), 7.49 (t, J=7.6 Hz, 1H), 5.90 (s, 1H), 3.66 (s, 1H), 3.37-3.47 (m, 9H), 3.17 (d, J=4.9 Hz, 1H), 2.82 (s, 3H), 2.07 (s, 1H), 1.91 (s, 1H), 1.79 (s, 1H), 1.60 (s, 1H).

EXAMPLE 23

2-(1-cyclopropylmethylpiperidin-3-yl)-4H-pyrazolo[1,5-a]quinazolin-5-one

The title compound was prepared as the trifluoroacetate salt as described in EXAMPLE 20, substituting cyclopropanecarbaldehyde for formaldehyde. $^1$H NMR (CD$_3$OD) δ 8.23 (dd, J=8.0, 1.5 Hz, 1H), 8.14 (d, J=8.3 Hz, 1H), 7.86 (td, J=7.8, 1.5 Hz, 1H), 7.46-7.51 (m, 1H), 5.95 (s, 1H), 3.74 (s, 1H), 3.32-3.42 (m, 3H), 3.07 (d, J=7.4 Hz, 3H), 2.20 (d, J=7.4 Hz, 1H), 2.05 (s, 1H), 1.85-1.97 (m, 2H), 1.14-1.24 (m, 1H), 0.74-0.84 (m, 2H), 0.41-0.50 (m, 2H).

EXAMPLE 24

2-[1-(3-piperidin-1-ylpropionyl)piperidin-3-yl]-4H-pyrazolo[1,5-a]quinazolin-5-one A solution of EXAMPLE 19 (0.1 g, 0.4 mmol), 3-piperidin-1-ylpropionic acid (0.06 g, 0.4 mmol), 1-hydroxybenzotriazole (0.098 g, 0.7 mmol), benzotriazol-1-yl-oxytripyrrolidinophosphonium hexafluorophosphate (0.377 g, 0.7 mmol) and diisopropylethylamine (0.4 mL, 2.2 mmol) in N,N'-dimethylformamide (4 mL) was heated in a microwave at 150° C. for 10 minutes. The mixture was concentrated and purified by HPLC on a C18 column with 0-100% acetonitrile/water/0.1% trifluoroacetic acid to provide the title compound as the trifluoroacetate salt. $^1$H NMR (CD$_3$OD) δ 8.20-8.26 (m, 1H), 8.11 (dd, J=8.3, 4.6 Hz, 1H), 7.83-7.89 (m, 1H), 7.44-7.50 (m, 1H), 5.92 (d, J=11.0 Hz, 1H), 4.65-4.79 (m, 1H), 4.08-4.14 (m, 1H), 4.01-4.05 (m, 1 H), 3.48-3.59 (m, 5H), 3.35-3.42 (m, 2H), 2.92-3.04 (m, 5H), 2.16-2.23 (m, 1H), 1.84-1.95 (m, 4H), 1.73-1.82 (m, 2H), 1.49-1.60 (m, 1H).

EXAMPLE 25

2-(1-propylpiperidin-3-yl)-4H-pyrazolo[1,5-a]quinazolin-5-one

The title compound was prepared as described in EXAMPLE 20, substituting propionaldehyde for formaldehyde. The crude product was purified by flash chromatography on silica gel with 0-10% methanol/dichloromethane/0.1% ammonium hydroxide. $^1$H NMR (CD$_3$OD) δ 8.23 (d, J=8.0, Hz, 1H), 8.13 (d, J=8.0 Hz, 1H), 7.87 (t, J=7.4 Hz, 1H), 7.49 (t, J=7.7 Hz, 1H), 5.96 (s, 1H), 3.47-3.57 (m, 1H), 3.34-3.43 (m, 1H), 3.14 (t, J=8.1 Hz, 4H), 2.14-2.26 (m, 1H), 1.83-1.94 (m, 4H), 1.14-1.24 (m, 1H), 1.07 (t, J=7.2 Hz, 4H).

EXAMPLE 26

2-(1-benzylpiperidin-3-yl)-4H-pyrazolo[1,5-a]quinazolin-5-one

The title compound was prepared as described in EXAMPLE 20, substituting benzaldehyde for formaldehyde. HPLC purification was followed by flash chromatography on silica gel with 0-10% methanol/dichloromethane/0.1% ammonium hydroxide. $^1$H NMR (CD$_3$OD) δ 8.21 (dd, J=8.0, 1.5 Hz, 1H), 8.06 (d, J=8.3 Hz, 1H), 7.82-7.88 (m, 1H), 7.35-7.46 (m, 6H), 5.87 (s, 1H), 3.84-3.93 (m, 2H), 3.09-3.18 (m, 2H), 2.67 (s, 1H), 2.48-2.57 (m, 1H), 2.07-2.14 (m, 1H), 1.79-1.91 (m, 2H), 1.68 (s, 1H).

EXAMPLE 27

2-(1-cyclopentylmethylpiperidin-3-yl)-4H-pyrazolo[1,5-a]quinazolin-5-one

The title compound was prepared as described in EXAMPLE 20, substituting cyclopentanecarboxaldehyde for formaldehyde. HPLC purification was followed by flash chromatography on silica gel with 0-10% methanol/dichloromethane/0.1% ammonium hydroxide. $^1$H NMR (CD$_3$OD) δ 8.21 (d, J=8.0, Hz, 1H), 8.11 (d, J=7.7 Hz, 1H), 7.82-7.87 (m, 1H), 7.45 (t, J=8.1 Hz, 1H), 5.88 (s, 1H), 3.19-3.25 (m, 1H), 3.01-3.11 (m, 2H), 2.47 (d, J=7.1 Hz, 2H), 2.32 (s, 1H), 2.17 (dt, J=15.1, 7.6 Hz, 2H), 2.07 (dd, J=13.0, 3.8 Hz, 1H), 1.78-1.87 (m, 4H), 1.61-1.70 (m, 2H), 1.52-1.61 (m, 3H), 1.19-1.29 (m, 2H).

EXAMPLE 28

2-(1-pyridin-4-ylmethylpiperidin-3-yl)-4H-pyrazolo[1,5-a]quinazolin-5-one

The title compound was prepared as described in EXAMPLE 20, substituting pyridine-4-carboxaldehyde for formaldehyde. HPLC purification was followed by flash chromatography on silica gel with 0-10% methanol/dichloromethane/0.1% ammonium hydroxide. $^1$H NMR (CD$_3$OD) δ 8.45-8.50 (m, 2H), 8.20 (dd, J=8.0, 1.5 Hz, 1H), 8.08 (d, J=7.3 Hz, 1H), 7.78-7.86 (m, 1H), 7.42-7.48 (m, 3H), 5.86 (s, 1H), 3.64 (s, 1H), 3.49 (q, J=7.06 Hz, 1H), 3.01-3.10 (m, 2H), 2.87 (s, 1H), 2.24-2.31 (m, 1H), 2.17 (td, J=11.1, 3.5 Hz, 1H), 2.05 (s, 1H), 1.74-1.86 (m, 2H), 1.58 (d, J=12.6 Hz, 1H).

EXAMPLE 29

2-(1-isopropylpiperidin-3-yl)-4H-pyrazolo[1,5-a]quinazolin-5-one

A solution of EXAMPLE 19 (0.07 g, 0.3 mmol) and 2-iodopropane (0.09 mL, 0.9 mmol) in dioxane (2 mL) and was treated with sodium hydride (0.01 g, 0.4 mmol). The mixture was stirred overnight at 65° C., cooled to ambient temperature, treated with water and concentrated. The residue was purified by flash chromatography on silica gel with 10% methanol/dichloromethane to provide the title compound. $^1$H NMR (CD$_3$OD) δ 8.21 (dd, J=8.0, 1.5 Hz, 1H), 8.11 (d, J=8.0 Hz, 1H), 7.81-7.87 (m, 1H), 7.42-7.47 (m, 1H), 5.88 (s, 1H), 3.21 (dt, J=11.3, 1.9, 1H), 2.99-3.10 (m, 2H), 2.92 (dt, J=13.2, 6.6 Hz, 1H), 2.51 (t, J=11.0 Hz, 1H), 2.38 (td, J=11.5, 2.8 Hz, 1H), 2.09 (ddd, J=9.0, 3.8, 3.7 Hz, 1H), 1.83-1.92 (m, 1H), 1.70-1.82 (m, 1H), 1.59 (qd, J=12.3, 4.0 Hz, 1H), 1.14-1.19 (m, 6H).

EXAMPLE 30

Methyl 4-(5-oxo-4,5-dihydropyrazolo[1,5-a]quinazolin-2-yl)benzoate

The title compound was prepared as described in EXAMPLE 1, substituting methyl 4-(2-cyanoacetyl)benzoate for 3-oxo-2-phenylpropionitrile. $^1$H NMR (DMSO-$d_6$) δ 12.37 (s, 1H), 8.11-8.21 (m, 4H) 8.04-8.08 (m, 2H), 7.89-7.98 (m, 1H), 7.53 (t, J=7.6 Hz, 1H), 6.50 (s, 1H), 3.89 (s, 3H).

EXAMPLE 31

2-(3-fluoro-4-morpholin-4-ylphenyl)-4H-pyrazolo[1,5-a]quinazolin-5-one

The title compound was prepared as described in EXAMPLE 1, substituting 3-(3-fluoro-4-morpholin-4-ylphenyl)-3-oxo-propionitrile for 3-oxo-2-phenylpropionitrile. $^1$H NMR (DMSO-$d_6$) δ 12.30 (s, 1H), 8.15 (d, J=8.1 Hz, 2H), 7.86-7.95 (m, 1H), 7.69-7.78 (m, 2H), 7.49 (t, J=7.8 Hz, 1H), 7.11 (t, J=8.6 Hz, 1H), 6.37 (s, 1H), 3.77 (s, 4H), 3.09 (d, J=4.1 Hz, 4H).

EXAMPLE 32

2-cyclopropyl-4H-pyrazolo[1,5-a]quinazolin-5-one

EXAMPLE 32A 3-cyclopropyl-3-oxopropionitrile

A solution of acetonitrile (0.25 mL, 4.8 mmol) in tetrahydrofuran (3 mL) was cooled to −78° C. and treated with 1.6 M n-butyl lithium in hexanes (3 mL, 4.8 mmol). The mixture was stirred at −78° C. for 2 hours and a solution of cyclopropanecarbonyl chloride (0.22 mL, 2.4 mmol) in tetrahydrofuran (1 mL) was added. The mixture was stirred for 1 hour and 20% hydrochloric acid was added until the pH=3. The mixture was diluted with ethyl acetate, washed with water and brine, filtered through silica gel and concentrated to provide the title compound.

EXAMPLE 32B 2-cyclopropyl-4H-pyrazolo[1,5-a]quinazolin-5-one

The title compound was prepared as described in EXAMPLE 1, substituting EXAMPLE 32A for 3-oxo-2-phenylpropionitrile. $^1$H NMR (DMSO-$d_6$) δ 12.07 (s, 1H), 8.10 (dd, J=8.0, 1.5 Hz, 1H), 7.98 (d, J=7.7 Hz, 1H), 7.84 (td, J=7.8, 1.5 Hz, 1H), 7.39-7.47 (m, 1H), 5.62 (s, 1H), 1.95-2.03 (m, 1H), 0.96 (ddd, J=8.3, 6.4, 4.0 Hz, 2H), 0.78 (ddd, J=7.0, 4.5, 4.1 Hz, 2H).

EXAMPLE 33

2-(1-benzylpiperidin-4-yl)-4H-pyrazolo[1,5-a]quinazolin-5-one

EXAMPLE 33A 3-(1-benzylpiperidin-4-yl)-3-oxo-propionitrile

The title compound was prepared as described in EXAMPLE 32A, substituting methyl 1-benzylpiperidin-4-carboxylate for cyclopropanecarbonyl chloride.

EXAMPLE 33B 2-(1-benzylpiperidin-4-yl)-4H-pyrazolo[1,5-a]quinazolin-5-one

The title compound was prepared as described in EXAMPLE 1, substituting EXAMPLE 33A for 3-oxo-2-phenylpropionitrile. $^1$H NMR (CD$_3$OD) δ 8.22 (d, J=7.8 Hz, 1H), 8.06 (s, 1H), 7.81-7.89 (m, 1H), 7.45-7.56 (m, 6H), 5.89 (s, 1H), 4.36 (s, 2H), 3.51-3.65 (m, 2H), 3.13-3.29 (m, 2H), 2.25-2.29 (m, 2H), 1.96-2.11 (m, 1H).

EXAMPLE 34

N-[3-(5-oxo-4,5-dihydropyrazolo[1,5-a]quinazolin-2-yl)phenyl]-3-piperidin-1-ylpropionamide A solution of EXAMPLE 12 (0.1 g, 0.4 mmol), 3-piperidinopropionic acid (60 mg, 0.4 mmol), 1-hydroxybenzotriazole (0.098 g, 0.7 mmol), benzotriazol-1-yl-oxytripyrrolidinophosphonium hexafluorophosphate (0.377 g, 0.7 mmol) and diisopropylethylamine (0.4 mL, 2.2 mmol) in N,N'-dimethylformamide (4 mL) was heated in a microwave at 100° C. for 15 minutes. The mixture was concentrated and purified by flash chromatography on silica gel with 10% methanol/dichloromethane to provide the title compound. $^1$H NMR (CD$_3$OD) δ 8.23-8.27 (m, 3H), 7.89 (td, J=7.8, 1.5 Hz, 1H), 7.68 (d, J=8.3 Hz, 1H), 7.59 (dd, J=7.1, 2.2 Hz, 1H), 7.48-7.56 (m, 1H), 7.42 (t, J=8.0 Hz, 1H), 6.33 (s, 1H), 3.62 (s, 2H), 3.51 (t, J=6.6 Hz, 2H), 3.04 (s, 2H), 2.96 (t, J=6.8 Hz, 2H), 1.98 (d, J=3.4 Hz, 2H), 1.82 (s, 3H), 1.58 (s, 1H).

EXAMPLE 35

2-piperidin-4-yl-4H-pyrazolo[1,5-a]quinazolin-5-one

A mixture of EXAMPLE 33 (0.15 g, 0.4 mmol) and 10% palladium on carbon (0.02 g) in methanol (5 mL) was stirred overnight under 1 atmosphere hydrogen and filtered. The filtrate was concentrated and the residue purified by flash chromatography on silica gel with 10% methanol/dichloromethane to provide the title compound. $^1$H NMR (CD$_3$OD) δ 8.22 (dd, J=7.9, 1.2 Hz, 1H), 8.11 (d, J=8.2 Hz, 1H), 7.83-7.88 (m, 1H), 7.47 (t, J=7.6 Hz, 1H), 5.91 (s, 1H), 3.50 (dt, J=13.0, 3.7 Hz, 2H), 3.12-3.19 (m, 2H), 2.29 (dd, J=15.0, 3.4 Hz, 2H), 1.99-2.08 (m, 2H).

EXAMPLE 36

2-(4-pyrrolidin-1-ylmethylphenyl)-4H-pyrazolo[1,5-a]quinazolin-5-one

The title compound was prepared as described in EXAMPLE 1, substituting 3-oxo-3-(4-pyrrolidin-1-ylmethylphenyl)propionitrile for 3-oxo-2-phenylpropionitrile. $^1$H NMR (CD$_3$OD) δ 8.22-8.29 (m, 2H), 8.07 (d, J=8.2 Hz, 2H), 7.89-7.93 (m, 1H), 7.62 (d, J=8.2 Hz, 2H), 7.52 (t, J=7.2 Hz, 1H), 6.40 (s, 1H), 4.43 (s, 2H), 3.50-3.57 (m, 2H), 3.19-3.27 (m, 2H), 2.18-2.25 (m, 2H), 1.98-2.07 (m, 2H).

EXAMPLE 37

2-(1-methylpiperidin-4-yl)-4H-pyrazolo[1,5-a]quinazolin-5-one

The title compound was prepared as described in EXAMPLE 20, substituting EXAMPLE 35 for EXAMPLE 19. The crude product was purified by flash chromatography on silica gel with 0-10% methanol/dichloromethane/0.1% ammonium hydroxide. $^1$H NMR (DMSO-d$_6$) δ 12.12 (s, 1H), 8.12 (d, J=7.1 Hz, 1H), 8.01 (d, J=8.0 Hz, 1H), 7.83-7.87 (m, 1H), 7.43-7.47 (m, 1H), 5.79 (s, 1H), 2.98-3.07 (m, 2H), 2.67-2.77 (m, 1H), 2.38 (s, 5H), 1.95-2.02 (m, 2H), 1.72-1.83 (m, 2H).

EXAMPLE 38

2-(1-ethylpiperidin-4-yl)-4H-pyrazolo[1,5-a]quinazolin-5-one

The title compound was prepared as described in EXAMPLE 21, substituting EXAMPLE 35 for EXAMPLE 19. The crude product was purified by flash chromatography on silica gel with 0-10% methanol/dichloromethane/0.1% ammonium hydroxide. $^1$H NMR (DMSO-d$_6$) δ 12.18 (s, 1H), 8.13 (d, J=7.1 Hz, 1H), 8.01 (d, J=8.6 Hz, 1H), 7.87 (td, J=7.8, 1.5 Hz, 1H), 7.44-7.49 (m, 1H), 5.81 (s, 1H), 3.51 (s, 2H), 3.17 (d, J=5.2 Hz, 1H), 3.08 (s, 2H), 2.99 (s, 2H), 2.16 (s, 2H), 2.02 (s, 2H) 1.27 (s, 3H).

EXAMPLE 39

2-(1-propylpiperidin-4-yl)-4H-pyrazolo[1,5-a]quinazolin-5-one

The title compound was prepared as described in EXAMPLE 25, substituting EXAMPLE 35 for EXAMPLE 19. $^1$HNMR (DMSO-d$_6$) δ 8.12 (dd, J=7.8, 1.4 Hz, 1H), 8.01 (d, J=8.0 Hz, 1H), 7.84-7.88 (m, 1H), 7.44-7.48 (m, 1H), 5.81 (s, 1H), 3.15 (s, 1H), 2.85-2.90 (m, 4H), 2.04-2.13 (m, 2H), 1.88-1.99 (m, 3H), 1.65 (s, 2H), 0.91 (t, J=7.5 Hz, 4H).

EXAMPLE 40

2-(1-cyclopropylmethylpiperidin-4-yl)-4H-pyrazolo[1,5-a]quinazolin-5-one

The title compound was prepared as described in EXAMPLE 23, substituting EXAMPLE 35 for EXAMPLE 19. The crude product was purified by flash chromatography on silica gel with 0-10% methanol/dichloromethane/0.1% ammonium hydroxide. $^1$H NMR (DMSO-d$_6$) δ 12.18 (s, 1H), 8.11-8.14 (m, 1H), 8.01 (d, J=8.0 Hz, 1H), 7.84-7.88 (m, 1H), 7.46 (d, J=7.5 Hz, 1H), 5.81 (s, 1H), 3.15-3.25 (m, 4H), 2.76-2.86 (m, 1H), 2.56-2.67 (m, 1H), 1.99-2.10 (m, 2H), 1.83-1.93 (m, 3H), 0.98 (s, 1H) 0.54 (s, 2H), 0.24 (s, 2H).

EXAMPLE 41

2-(1-isobutylpiperidin-4-yl-4H-pyrazolo[1,5-a]quinazolin-5-one

The title compound was prepared as described in EXAMPLE 22, substituting EXAMPLE 35 for EXAMPLE 19. The crude product was purified by flash chromatography on silica gel with 0-10% methanol/dichloromethane/0.1% ammonium hydroxide. $^1$H NMR (DMSO-d$_6$) δ 12.15 (s, 1H), 8.13 (d, J=6.8 Hz, 1H), 8.00 (d, J=8.3 Hz, 1H), 7.84-7.89 (m, 1H), 7.46 (t, J=7.1 Hz, 1H), 5.81 (s, 1H), 3.56 (s, 1H), 3.17 (d, J=5.2 Hz, 1H), 2.90-3.01 (m, 4H), 2.12 (s, 3H), 2.07 (s, 2H), 1.86-1.94 (m, 1H), 0.97 (s, 6H).

EXAMPLE 42

2-(1-isopropylpiperidin-4-yl-4H-pyrazolo[1,5-a]quinazolin-5-one

The title compound was prepared as described in EXAMPLE 28, substituting EXAMPLE 35 for EXAMPLE 19. $^1$H NMR (CD$_3$OD) δ 8.22 (d, J=8.0 Hz, 1H), 8.11 (d, J=8.3 Hz, 1H), 7.82-7.88 (m, 1H), 7.47 (t, J=7.7 Hz, 1H), 5.91 (s, 1H), 3.48-3.58 (m, 4H), 3.22 (s, 2H), 2.34 (s, 2H), 2.14 (s, 2H), 1.39 (d, J=6.8 Hz, 7H).

EXAMPLE 43

2-pyrrolidin-3-yl-4H-pyrazolo[1,5-a]quinazolin-5-one

EXAMPLE 43A

Benzyl 3-(2-cyanoacetyl)pyrrolidine-1-carboxylate

A mixture of benzyl 3-carbomethoxypyrrolidine-1-carboxylate (1 g, 4 mmol) and thionyl chloride (5 mL) was heated at reflux for 10 minutes and stirred overnight at ambient temperature. The mixture was concentrated, dried and substituted for cyclopropanecarbonyl chloride in EXAMPLE 32A to provide the title compound.

EXAMPLE 43B 2-pyrrolidin-3-yl-4H-pyrazolo[1,5-a]quinazolin-5-one

The title compound was prepared as described in EXAMPLE 1, substituting EXAMPLE 43A for 3-oxo-2-phenylpropionitrile. $^1$H NMR (CD$_3$OD) δ 8.21-8.24 (m, 1H), 8.15 (d, J=8.3 Hz, 1H), 7.86 (td, J=7.8, 1.5 Hz, 1H), 7.46-7.51 (m, 1H), 5.97 (s, 1H), 3.73-3.79 (m, 1H), 3.66 (d, J=6.8 Hz, 2H), 3.50 (s, 1H), 3.42-3.47 (m, 1H), 2.46-2.52 (m, 1H), 2.27-2.33 (m, 1H).

EXAMPLE 44

Benzyl 3-(5-oxo-4,5-dihydropyrazolo[1,5-a]quinazolin-2-yl)pyrrolidine-1-carboxylate The filtrate from EXAMPLE 43B was concentrated and purified by flash chromatography on silica gel with 10% methanol/dichloromethane to provide the title compound. $^1$H NMR (DMSO-d$_6$) δ 8.11 (s, 1H), 7.99 (s, 1H), 7.84 (s, 1H), 7.44 (s, 1H), 7.33 (s, 5H), 5.85 (s, 1H), 5.08 (s, 2H), 3.75 (s, 1H), 3.49 (s, 1H), 2.27 (s, 1H), 2.09 (s, 1H).

EXAMPLE 45

2-(1-methylpyrrolidin-3-yl)-4H-pyrazolo[1,5-a]quinazolin-5-one

The title compound was prepared as described in EXAMPLE 20, substituting EXAMPLE 43B for EXAMPLE 19. The crude product was purified by flash chromatography on silica gel with 0-10% methanol/dichloromethane/0.1% ammonium hydroxide. $^1$H NMR (CD$_3$OD) δ 8.22 (dd, J=7.8, 1.7 Hz, 1H), 8.14 (d, J=8.3 Hz, 1H), 7.86 (td, J=7.8, 1.5 Hz, 1H), 7.45-7.51 (m, 1H), 5.97 (s, 1H), 3.81-3.89 (m, 1H), 3.66-3.74 (m, 2H), 3.44-3.56 (m, 2H), 3.00 (s, 3H), 2.54-2.64 (m, 1H), 2.36 (ddd, J=14.9, 13.4, 6.8 Hz, 1H).

EXAMPLE 46

2-(1-ethylpyrrolidin-3-yl)-4H-pyrazolo[1,5-a]quinazolin-5-one

The title compound was prepared as described in EXAMPLE 21, substituting EXAMPLE 43B for EXAMPLE 19. The crude product was purified by flash chromatography on silica gel with 0-10% methanol/dichloromethane/0.1% ammonium hydroxide. $^1$H NMR (CD$_3$OD) δ 8.18-8.24 (m, 1H), 8.10 (d, J=8.2 Hz, 1H), 7.81-7.88 (m, 1H), 7.46 (t, J=7.6 Hz, 1H), 5.92 (s, 1H), 3.57-3.65 (m, 1H), 3.28 (s, 1H), 3.00-3.08 (m, 1H), 2.87-2.97 (m, 2H), 2.75-2.84 (m, 2H), 2.36-2.44 (m, 1H), 2.16 (td, J=13.8, 7.2 Hz, 1H), 1.18-1.25 (m, 3H).

EXAMPLE 47

2-(1-cyclopropylmethylpyrrolidin-3-yl)-4H-pyrazolo[1,5-a]quinazolin-5-one

The title compound was prepared as described in EXAMPLE 23, substituting EXAMPLE 43B for EXAMPLE 19. The crude product was purified by flash chromatography on silica gel with 0-10% methanol/dichloromethane/0.1% ammonium hydroxide. $^1$H NMR (CD$_3$OD) δ 8.21 (dd, J=8.0, 1.5 Hz, 1H), 8.10 (d, J=8.3 Hz, 1H), 7.82-7.87 (m, 1H), 7.45 (t, J=7.7 Hz, 1H), 5.92 (s, 1H), 3.54-3.62 (m, 1H), 3.28 (d, J=8.3 Hz, 2H), 3.01 (ddd, J=9.74 7.8, 6.1 Hz, 1H), 2.78-2.85 (m, 3H), 2.33-2.40 (m, 1H), 2.08-2.17 (m, 1H), 0.92-1.02 (m, 1H), 0.53-0.60 (m, 2H), 0.17-0.24 (m, 2H).

EXAMPLE 48

2-piperidin-2-yl-4H-pyrazolo[1,5-a]quinazolin-5-one

EXAMPLE 48A

Benzyl 2-(2-cyanoacetyl)piperidine-1-carboxylate

The title compound was prepared as described in EXAMPLE 43A, substituting benzyl-2-carbomethoxypiperidin-1-carboxylate for benzyl 3-carbomethoxypyrrolidine-1-carboxylate.

EXAMPLE 48B 2-piperidin-2-yl-4H-pyrazolo[1,5-a]quinazolin-5-one

The title compound was prepared as described in EXAMPLE 1, substituting EXAMPLE 48A for 3-oxo-2-phenylpropionitrile. $^1$H NMR (CD$_3$OD) δ 8.18-8.27 (m, 2H), 7.87-7.92 (m, 1H), 7.50-7.56 (m, 1H), 6.07 (s, 1H), 4.46 (dd, J=11.8, 3.2 Hz, 1H), 3.49 (s, 2H), 3.19 (td, J=12.6, 3.1 Hz, 1H), 2.29-2.37 (m, 1H), 1.94-2.04 (m, 3H), 1.75-1.85 (m, 2H).

EXAMPLE 49

2-(1-methylpiperidin-2-yl)-4H-pyrazolo[1,5-a]quinazolin-5-one

The title compound was prepared as described in EXAMPLE 20, substituting EXAMPLE 48B for EXAMPLE 19. The crude product was purified by flash chromatography on silica gel with 0-10% methanol/dichloromethane/0.1% ammonium hydroxide. $^1$H NMR (CD$_3$OD) δ 8.24 (dd J=7.9, 1.2 Hz, 1H), 8.15 (d, J=8.2 Hz, 1H), 7.85-7.90 (m, 1H), 7.50 (t, J=7.6 Hz, 1H), 6.05 (s, 1H), 3.55-3.63 (m, 1H), 3.49 (q, J=7.0 Hz, 1H), 3.24-3.30 (m, 1H), 2.60 (td, J=12.0, 3.5 Hz, 1H), 2.4 (s, 3H), 1.90-1.94 (m, 2H), 1.82-1.89 (m, 2H), 1.52-1.62 (m, 1H), 1.18 (t, J=7.0 Hz, 1H).

EXAMPLE 50

(S)-2-acetylamino-4-methyl-N-(5-oxo-4,5-dihydropyrazolo[1,5-a]quinazolin-3-ylmethyl)pentanamide

EXAMPLE 50A 3-aminomethyl-4H-pyrazolo[1,5-a]quinazolin-5-one

A suspension of 1.5 g of 3-cyano-4H-pyrazolo[1,5-a]quinazolin-5-one in 150 mL of 20% ammonia in methanol was shaken with 15 g of aqueous Raney nickel at ambient temperature under 60 psi of hydrogen for 70 minutes. The suspension was diluted with 150 mL of methanol and warmed to dissolve the precipitated product. Filtration through a nylon membrane and concentration of the filtrate yielded the title compound. MS (ESI) m/z 198 (M+H—NH$_3$)$^+$.

EXAMPLE 50B (S)-2-acetylamino-4-methyl-N-(5-oxo-4,5-dihydropyrazolo[1,5-a]quinazolin-3-ylmethyl)pentanamide To a microwave vial containing 125 mg of polystyrene-1,3-dicyclohexylcarbodiimide resin (Argonaut Technologies, 1.2 mmol/g) was added N-acetyl-L-leucine (10.4 mg, 0.06 mmol) in N,N'-dimethylacetamide (0.3 mL). A solution of 1-hydroxybenzotriazole (6.8 mg, 0.05 mmol) in N,N'-dimethylacetamide (0.7 mL) was added, followed by the addition of diisopropylethylamine (27.7 μL, 0.15 mmol) in N,N'-dimethylacetamide (0.7 mL), and EXAMPLE 50A (11.2 mg, 0.05 mmol) in N,N'-dimethylacetamide (1 mL). The mixture was heated in a microwave at 130° C. for 10 minutes, MP-carbonate (macroporous polystyrene anion-exchange resin, Argonaut Technologies) was added and the mixture shaken overnight. The mixture was filtered, concentrated and the residue dissolved in 1:1 dimethylsulfoxide/methanol and purified by HPLC on a C18 column with 0-100% acetonitrile/water/0.1% trifluoroacetic acid to give the title compound. $^1$H NMR (DMSO-d$_6$) δ 0.80 (d, 3H), 0.87 (d, 3H), 1.43 (t, 2H), 1.49-1.60 (m, 1H), 1.83-1.88 (m, 3H), 4.17-4.21 (m, 2H), 4.24 (t, 1H), 7.51 (t, 1H), 7.65-7.73 (m, 1H), 7.91 (t, 1H), 8.07 (d, 1H), 8.16 (d, 1H).

EXAMPLE 51

(R)-2-methoxy-N-(5-oxo-4,5-dihydropyrazolo[1,5-a]quinazolin-3-ylmethyl)-2-phenylacetamide The title compound was prepared as described in EXAMPLE 50 using (R)-(−)-α-methoxyphenylacetic acid in place of N-acetyl-L-leucine. $^1$H NMR (DMSO-$d_6$) δ 3.24-3.32 (m, 3H), 4.21-4.25 (m, 2H), 4.61-4.70 (m, 1H), 7.27-7.39 (m, 5H), 7.51 (t, 1H), 7.62-7.67 (m, 1H), 7.90 (t, 1H), 8.06 (d, 1H), 8.16 (d, 1H).

EXAMPLE 52

N-(5-oxo-4,5-dihydropyrazolo[1,5-a]quinazolin-3-ylmethyl)isonicotinamide

The title compound was prepared as the trifluoroacetate salt as described in EXAMPLE 50 using pyridine-4-carboxylic acid in place of N-acetyl-L-leucine. $^1$H NMR (DMSO-$d_6$) δ 4.46-4.48 (m, 2H), 7.55 (t, 1H), 7.73-7.76 (m, 1H), 7.76-7.79 (m, 2H), 7.82-7.84 (m, 1H), 7.93 (t, 1H), 8.10 (d, 1H), 8.19 (d, 1H), 8.68-8.71 (m, 1H), 8.71-8.75 (m, 2H).

EXAMPLE 53

N-(5-oxo-4,5-dihydropyrazolo[1,5-a]quinazolin-3-ylmethyl)-3-piperidin-1-yl-propionamide The title compound was prepared as the trifluoroacetate salt as described in EXAMPLE 50 using 3-piperidinopropionic acid in place of N-acetyl-L-leucine. $^1$H NMR (DMSO-$d_6$) δ 0.99-1.97 (m, 6 H), 2.60-2.63 (m, 1H), 2.67 (t, 1H), 2.80-3.03 (m, 2H), 3.30 (t, 2H), 3.34-3.53 (m, 2H), 4.20-4.33 (m, 2H), 7.51-7.66 (m, 1H), 7.79-7.84 (m, 1H), 7.89-8.03 (m, 1H), 8.12 (d, 1H), 8.22 (d, 1H).

EXAMPLE 54

N-(5-oxo-4,5-dihydropyrazolo[1,5-a]quinazolin-3-ylmethyl)-3-pyrrolidin-1-yl-propionamide The title compound was prepared as the trifluoroacetate salt as described in EXAMPLE 50 using 3-pyrrolidinopropionic acid in place of N-acetyl-L-leucine. $^1$H NMR (DMSO-$d_6$) δ 1.77-1.95 (m, 2H), 1.99-2.11 (m, 2H), 2.58-2.60 (m, 1H), 2.63 (t, 1H), 2.95-3.06 (m, 2H), 3.36 (t, 2H), 3.46-3.59 (m, 2H), 4.24-4.31 (m, 2H), 7.47-7.63 (m, 1H), 7.77-7.82 (m, 1H), 7.90-7.98 (m, 1H), 8.05-8.15 (m, 1H), 8.15-8.23 (m, 1H).

EXAMPLE 55

2-morpholin-4-yl-N-(5-oxo-4,5-dihydropyrazolo[1,5-a]quinazolin-3-ylmethyl)acetamide The title compound was prepared as the trifluoroacetate salt as described in EXAMPLE 50 using morpholin-4-yl-acetic acid in place of N-acetyl-L-leucine. $^1$H NMR (DMSO-$d_6$) δ 2.97-3.34 (m, 4H), 3.65-3.95 (m, 6H), 4.26-4.38 (m, 2H), 7.53 (t, 1H), 7.75-7.83 (m, 1H), 7.92 (t, 1H), 8.08 (d, 1H), 8.20 (d, 1H).

EXAMPLE 56

3-morpholin-4-yl-N-(5-oxo-4,5-dihydropyrazolo[1,5-a]quinazolin-3-ylmethyl)-propionamide The title compound was prepared as the trifluoroacetate salt as described in EXAMPLE 50 using 3-morpholinopropionic acid in place of N-acetyl-L-leucine. $^1$H NMR (DMSO-$d_6$) δ 2.58-2.60 (m, 1H), 2.64 (t, 2H), 2.78-3.96 (m, 9H), 4.23-4.31 (m, 2H), 7.54 (t, 1H), 7.74-7.82 (m, 1H), 7.93 (t, 1H), 8.08 (d, 1H), 8.18 (d, 1H).

EXAMPLE 57

2-phenethyl-4H-pyrazolo[1,5-a]quinazolin-5-one

EXAMPLE 57A 3-oxo 5-phenyl-pentanenitrile

A solution of cyanoacetic acid (1.0 g, 11.8 mmol) in tetrahydrofuran (20 mL) was cooled to −78° C. and treated with 1.6 M n-butyl lithium in hexanes (14.7 mL, 23.5 mmol). The mixture was warmed to −20° C. over 2 hours, cooled to −78° C. and treated with 3-phenylpropionyl chloride (prepared by refluxing a solution of 3-phenylpropionic acid (1.0 g, 6.7 mmol) in thionyl chloride (4 mL) for 3 hours, evaporating and drying). The mixture was stirred at −78° C. for 1 hour and 20% hydrochloric acid added until the pH=3. The mixture was diluted with diethyl ether, washed with saturated sodium bicarbonate, and the organic layer separated and concentrated. The crude product was purified by flash chromatography on silica gel using 0-50% ethyl acetate/hexanes to provide the title compound. MS (ESI) m/e 191 (M+H+NH$_3$).

EXAMPLE 57B 2-phenethyl-4H-pyrazolo[1,5-a]quinazolin-5-one

A mixture of 2-hydrazinobenzoic acid (0.17 g, 0.9 mmol) and EXAMPLE 57A (0.155 g, 0.9 mmol) in acetic acid (3 mL) was heated in a microwave at 150° C. for 10 minutes. The precipitated product was washed with methanol and diethyl ether and dried. $^1$H NMR (DMSO-$d_6$) δ 12.10 (s, 1H), 8.09-8.14 (m, 1H), 8.02 (d, J=7.9 Hz, 1H), 7.82-7.88 (m, 1H), 7.44 (t, J=7.6 Hz, 1H), 7.26-7.32 (m, 4H), 7.16-7.22 (m, 1H), 5.78 (s, 1H), 2.92-3.01 (m, 4H).

EXAMPLE 58

2-benzyl-4H-pyrazolo[1,5-a]quinazolin-5-one

EXAMPLE 58A 3-oxo-4-phenyl-butyronitrile

The title compound was prepared as described in EXAMPLE 57A, substituting phenylacetyl chloride for 3-phenylpropionyl chloride. MS (ESI) m/e 177 (M+H+NH$_3$)$^+$.

EXAMPLE 58B 2-benzyl-4H-pyrazolo[1,5-a]quinazolin-5-one

The title compound was prepared as described in EXAMPLE 57B, substituting EXAMPLE 58A for EXAMPLE 57A. The crude product was purified by flash chromatography on silica gel with 50% ethyl acetate/hexanes. $^1$H NMR (DMSO-$d_6$) δ 8.11 (dd, J=7.9, 1.2 Hz, 1H), 8.04 (d, J=8.2 Hz, 1H), 7.82-7.89 (m, 1H), 7.42-7.49 (m, 1H), 7.29-7.33 (m, 4H), 7.22 (td, J=5.6, 2.8 Hz, 1H), 5.67 (s, 1H), 3.99 (s, 2H).

EXAMPLE 59

2-piperidin-4-ylmethyl-4H-pyrazolo[1,5-a]quinazolin-5-one

EXAMPLE 59A tert-butyl 4-(3-cyano-2-oxopropyl)piperidine-1-carboxylate

A solution of tert-butyl 4-carboxymethylpiperidine-1-carboxylate (1 g, 4.1 mmol) in tetrahydrofuran (5 mL) was treated with 1,1'-carbonyldiimidazole (0.67 g, 4.1 mmol). The mixture was heated at 55° C. for 2 hours, cooled and submitted to the conditions described in EXAMPLE 57A, substituting the solution obtained above for 3-phenylpropionyl chloride. MS (ESI) m/e 284 (M+H+NH$_3$)$^+$.

EXAMPLE 59B 2-piperidin-4-ylmethyl-4H-pyrazolo[1,5-a]quinazolin-5-one

The title compound was prepared as described in EXAMPLE 57B, substituting EXAMPLE 59A for EXAMPLE 57A. The crude product was purified by flash chromatography on silica gel with 10% methanol/dichloromethane/0.1% ammonium hydroxide. $^1$H NMR (DMSO-d$_6$) δ 8.11 (dd, J=7.9, 1.2 Hz, 1H), 8.00 (d, J=7.9 Hz, 1H), 7.78-7.85 (m, 1H), 7.43 (t, J=7.5 Hz, 1H), 5.72 (s, 1H), 3.35-3.39 (m, 1H), 3.17 (s, 1H), 2.91 (d, J=11.9 Hz, 2H), 2.40-2.49 (m, 3H), 1.65-1.74 (m, 1H), 1.60 (d, J=11.9 Hz, 2H), 1.05-1.14 (m, 2H).

EXAMPLE 60

2-(1-methylpiperidin-4-ylmethyl)-4H-pyrazolo[1,5-a]quinazolin-5-one

A solution of EXAMPLE 59 (0.034 g, 0.1 mmol) and 36% formaldehyde in water (0.05 mL, 0.6 mmol) in methanol (2 mL) was treated with sodium cyanoborohydride (0.006 g, 0.1 mmol) and acetic acid (0.2 mL). The mixture was stirred at ambient temperature for 2 hours and concentrated. The crude product was purified by flash chromatography on silica gel with 10% methanol/dichloromethane to provide the title compound. $^1$H NMR (DMSO-d$_6$) δ 8.11 (d, J=7.7 Hz, 1H), 8.01 (d, J=8.3 Hz, 1H), 7.81-7.86 (m, 1H), 7.44 (t, J=7.7 Hz, 1H), 5.74 (s, 1H), 2.72 (d, J=11.4 Hz, 2H), 2.54 (d, J=6.8 Hz, 2H) 2.13 (s, 3H), 1.82 (s, 2H), 1.54-1.66 (m, 3H), 1.18-1.29 (m, 2H).

EXAMPLE 61

2-(3-Bromobenzyl)pyrazolo[1,5-a]quinazolin-5(4H)-one

EXAMPLE 61A 4-(3-Bromophenyl)-3-oxobutanenitrile

The title compound was prepared as described in EXAMPLE 32A, substituting 2-(3-bromophenyl)acetyl) chloride-for cyclopropanecarbonyl chloride.

EXAMPLE 61B 2-(3-Bromobenzyl)pyrazolo[1,5-a]quinazolin-5(4H)-one

The title compound was prepared as described in EXAMPLE 1, substituting Example 61A for 3-oxo-2-phenylpropionitrile and using 3 mL of acetic acid. $^1$H NMR (400 MHz, DMSO-d$_6$) δ ppm 4.01 (s, 2 H) 5.73 (s, 1 H) 7.26-7.35 (m, 2 H) 7.41-7.48 (m, 2 H) 7.52-7.55 (m, 1 H) 7.86 (dd, J=8.29, 7.06 Hz, 1 H) 8.03 (d, J=7.67 Hz, 1 H) 8.12 (dd, J=7.98, 1.53 Hz, 1 H) 12.09 (s, 1 H).

EXAMPLE 62

3-[(5-Oxo-4,5-dihydropyrazolo[1,5-a]quinazolin-2-yl)methyl]benzonitrile

A mixture of Example 61B (0.075 g, 0.212 mmol), dicyanozinc (0.03 g, 0.254 mmol) and tetrakis(triphenylphosphine)palladium(0) (0.024 g, 0.021 mmol) in DMF (2 mL) was heated in a microwave (Personal Chemistry SmithSynthesizer) at 150° C. for 10 minutes. The mixture was evaporated and purified by chromatography on silica gel with 10% MeOH/CH$_2$Cl$_2$ to provide the desired product. $^1$H NMR (500 MHz, DMSO-d$_6$) δ ppm 4.08 (s, 2 H) 5.76 (s, 1 H) 7.46 (t, J=7.63 Hz, 1 H) 7.53 (t, J=7.63 Hz, 1 H) 7.69 (dd, J=12.36, 7.78 Hz, 2 H) 7.79-7.88 (m, 2 H) 8.02 (d, J=7.93 Hz, 1 H) 8.12 (d, J=7.93 Hz, 1 H) 12.12 (s, 1 H).

EXAMPLE 63

2-[3-(Aminomethyl)benzyl]pyrazolo[1,5-a]quinazolin-5(4H)-one

A mixture of Example 62 (0.32 g, 1.066 mmol) and 3 g raney-nickel in methanol ammonia (30 mL) was stirred under a hydrogen atmosphere at 60 psi for 3.5 hr. The mixture was filtered then evaporated and purified by chromatography on silica gel with 10% MeOH/CH$_2$Cl$_2$ to provide the desired product. $^1$H NMR (400 MHz, DMSO-d$_6$) δ ppm 3.17 (s, 1 H) 3.71 (s, 2 H) 3.97 (s, 2 H) 5.66 (s, 1 H) 7.14-7.20 (m, 2 H) 7.22-7.29 (m, 2 H) 7.42-7.47 (m, 1 H) 7.82-7.87 (m, 1 H) 8.03 (d, J=8.29 Hz, 1 H) 8.11 (dd, J=7.98, 1.53 Hz, 1 H).

EXAMPLE 64

2-(3-Pyridin-3-ylbenzyl)pyrazolo[1,5-a]quinazolin-5(4H)-one

A mixture of Example 61B (0.05 g, 0.141 mmol), pyridine-3-ylboronic acid (0.018 g, 0.148 mmol) cesium fluoride (0.064 g, 0.423 mmol) and tetrakis(triphenylphosphine)palladium(0) (0.1 g, 0.014 mmol) in DME (2 mL) was heated in a microwave (Personal Chemistry SmithSynthesizer) at 150° C. for 10 minutes. The mixture was filtered evaporated. The residue was purified by HPLC on a C18 column with 0-100% CH$_3$CN/H$_2$O/0.1% TFA to provide the desired product. $^1$H NMR (400 MHz, DMSO-d$_6$) δ ppm 4.10 (s, 2 H) 5.75 (s, 1 H) 7.41-7.51 (m, 3 H) 7.63-7.73 (m, 2 H) 7.76 (s, 1 H) 7.83-7.88 (m, 1 H) 8.04 (d, J=7.67 Hz, 1 H) 8.12 (dd, J=8.13, 1.38 Hz, 1 H) 8.35 (dt, J=7.98, 1.84 Hz, 1 H) 8.68 (dd, J=5.06, 1.38 Hz, 1 H) 9.01 (d, J=2.15 Hz, 1 H) 12.08 (s, 1 H).

EXAMPLE 65

2-[3-(2-Oxopyrrolidin-1-yl)benzyl]pyrazolo[1,5-a]quinazolin-5(4H)-one

A mixture of Example 61B (0.1 g, 0.282 mmol), pyrrolidin-2-one (0.048 g, 0.565 mmol) cesium carbonate (0.130 g, 0.395 mmol), tris(dibenzylideneacetone)dipalladium(0) (0.026 g, 0.028 mmol) and (9,9-dimethyl-9H-xanthene-4,5-diyl)bis(diphenylphosphine) (0.025 g, 0.043 mmol) in DME (2 mL) was heated in a microwave (Personal Chemistry SmithSynthesizer) at 200° C. for 60 minutes. The mixture was filtered evaporated. The residue was purified by chromatography on silica gel with 20% to 80% ethyl acetate in hexane to provide the desired product. $^1$H NMR (500 MHz, DMSO-$d_6$) δ ppm 2.01-2.08 (m, 2 H) 2.47 (t, J=8.09 Hz, 2 H) 3.81 (t, J=7.02 Hz, 2 H) 3.99 (s, 2 H) 5.67 (s, 1 H) 7.08 (d, J=7.63 Hz, 1 H) 7.30 (t, J=7.78 Hz, 1 H) 7.43-7.50 (m, 2 H) 7.66 (s, 1 H) 7.80-7.88 (m, 1 H) 8.04 (d, J=8.24 Hz, 1 H) 8.12 (d, J=7.93 Hz, 1 H).

EXAMPLE 66

3'-[(5-Oxo-4,5-dihydropyrazolo[1,5-a]quinazolin-2-yl)methyl]-1,1'-biphenyl-2-carbaldehyde The title compound was prepared as described in EXAMPLE 64, substituting 2-(formylphenyl)boronic acid- for pyridine-3-ylboronic acid. $^1$H NMR (500 MHz, DMSO-$d_6$) δ ppm 4.09 (s, 2 H) 5.75 (s, 1 H) 7.32 (d, J=7.02 Hz, 1 H) 7.40-7.49 (m, 4 H) 7.52 (d, J=7.63 Hz, 1 H) 7.56-7.61 (m, 1 H) 7.75 (d, J=1.22 Hz, 1 H) 7.85 (s, 1 H) 7.88-7.95 (m, 1 H) 8.04 (d, J=8.24 Hz, 1 H) 8.11 (dd, J=7.93, 1.53 Hz, 1 H) 9.90 (s, 1 H).

EXAMPLE 67

A-998677.0

2-[3-(2-Fluoropyridin-4-yl)benzyl]pyrazolo[1,5-a]quinazolin-5(4H)-one

A mixture of Example 61B (0.1 g, 0.282 mmol), 2-fluoro-4-(tributylstannyl)pyridine (0.11 g, 0.285 mmol) triethylamine (0.11 g, 1.1 mmol), tris(dibenzylideneacetone)dipalladium(0) (0.039 g, 0.01 mmol) and tri-o-tolylphosphine (0.007 g, 0.023 mmol) in DMF (2 mL) was heated at 100° C. for 6 hr. The mixture was diluted with EtOAc and washed with sat NaHCO$_3$, H$_2$O and brine, then evaporated. The residue was purified by chromatography on silica gel with 20% to 80% ethylacetate in hexane to provide the desired product. $^1$H NMR (500 MHz, DMSO-$d_6$) δ ppm 4.10 (s, 2 H) 5.75 (s, 1 H) 7.44-7.53 (m, 4 H) 7.68-7.74 (m, 2 H) 7.83-7.88 (m, 2 H) 8.04 (d, J=8.24 Hz, 1 H) 8.11 (d, J=6.71 Hz, 1 H) 8.30 (d, J=5.49 Hz, 1 H).

EXAMPLE 68

Methyl 3-[(5-oxo-4,5-dihydropyrazolo[1,5-a]quinazolin-2-yl)methyl]benzoate

A mixture of Example 61B (0.25 g, 0.706 mmol) triethylamine (0.2 ml, 1.542 mmol) and dichlorobis(diphenylphosphino)palladium(II) dichloromethane (0.03 g, 0.041 mmol) in methanol (10 mL) under carbon monoxide at 50 psi was heated at 100° C. for 3 hr. The mixture was filtered then evaporated and purified by chromatography on silica gel with 10% MeOH/CH$_2$Cl$_2$ to provide the desired product. $^1$H NMR (500 MHz, DMSO-$d_6$) δ ppm 3.81-3.86 (m, 3 H) 4.09 (s, 2 H) 5.71 (s, 1 H) 7.44-7.50 (m, 2 H) 7.62 (d, J=7.63 Hz, 1 H) 7.81-7.88 (m, 2 H) 7.91 (s, 1 H) 8.03 (d, J=7.63 Hz, 1 H) 8.12 (dd, J=7.93, 1.22 Hz, 1 H).

EXAMPLE 69

3-[(4-Methylpiperazin-1-yl)carbonyl]pyrazolo[1,5-a]quinazolin-5(4H)-one

EXAMPLE 69A

5-Oxo-4,5-dihydropyrazolo[1,5-a]quinazoline-3-carboxylic acid

A mixture of 2-hydrazinylbenzoic acid hydrochloride (1.05 g, 5.57 mmol), (E)-ethyl 2-cyano-3-ethoxyacrylate (0.9 g, 5.32 mmol) and sodium acetate (0.457 g, 5.57 mmol) in DMF (7 mL) was heated to 140° C. for 2 h then cooled. Water (5 mL) was added and the mixture was stirred at rt for 1 h then filtered. The solid was washed with H$_2$O, EtOH and Et$_2$O then dried. The solid was dissolved in EtOH (10 mL), treated with a 1M solution of sodium hydroxide (23 mL, 23 mmol) and the mixture was heated at 80° C. for 18 hr. The mixture was filtered hot then cooled and acidified with acetic acid and 10% HCl. The precipitated product was filtered, washed with H$_2$O and Et$_2$O, dried well and used without any further purification.

EXAMPLE 69B

3-[(4-Methylpiperazin-1-yl)carbonyl]pyrazolo[1,5-a]quinazolin-5(4H)-one

A mixture Example 69A (0.1 g, 0.44 mmol), 1-methyl piperazine (0.045 g, 0.45 mmol) and CDI (0.075 g, 0.53 mmol) in DMF (1 mL) and pyridine (1 mL) was stirred overnight at ambient temperature. The mixture was evaporated and purified by chromatography on silica gel with 10% MeOH/CH$_2$Cl$_2$ to provide the desired product. $^1$H NMR (500 MHz, DMSO-$d_6$) δ ppm 2.38 (s, 3 H) 2.58 (s, 4 H) 3.65-3.70 (m, 4 H) 7.15 (s, 1 H) 7.56 (t, J=7.48 Hz, 1 H) 7.88-7.96 (m, 1 H) 8.07 (s, 1 H) 8.12 (d, J=8.24 Hz, 1 H) 8.18 (d, J=7.02 Hz, 1 H).

EXAMPLE 70

3-(Pyrrolidine-1-carbonyl)pyrazolo[1,5-a]quinazolin-5(4H)-one

The title compound was prepared as described in Example 69B, substituting pyrrolidine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-$d_6$) δ ppm 1.85 (s, 2 H) 1.99 (s, 2 H) 3.50 (s, 2 H) 3.75 (s, 2 H) 7.59 (s, 1 H) 7.96 (s, 1 H) 8.14 (d, J=8.24 Hz, 1 H) 8.20 (d, J=7.93 Hz, 1 H) 8.25 (s, 1 H).

EXAMPLE 71

N,N-Dimethyl-5-oxo-4,5-dihydropyrazolo[1,5-a]quinazoline-3-carboxamide

The title compound was prepared as described in Example 69B, substituting dimethylamine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 3.32 (s, 6 H) 7.57 (t, J=7.48 Hz, 1 H) 7.92-7.97 (m, 1 H) 8.12-8.20 (m, 3 H) 11.32 (s, 1 H).

EXAMPLE 72

3-(Piperidine-1-carbonyl)pyrazolo[1,5-a]quinazolin-5(4H)-one

The title compound was prepared as described in Example 69B, substituting piperidine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 1.51-1.57 (m, 4 H) 1.60-1.67 (m, 2 H) 3.56-3.61 (m, 4 H) 7.56 (t, J=7.63 Hz, 1 H) 7.90-7.95 (m, 1 H) 8.04 (s, 1 H) 8.12 (d, J=7.93 Hz, 1 H) 8.15-8.20 (m, 1 H) 11.58 (s, 1 H).

EXAMPLE 73

N-Cyclopropyl-5-oxo-4,5-dihydropyrazolo[1,5-a]quinazoline-3-carboxamide

The title compound was prepared as described in Example 69B, substituting cyclopropylamine for 1-methyl piperazine in Example 69B. The mixture was evaporated and purified by chromatography on silica gel with 10% MeOH/CH$_2$Cl$_2$ to provide the desired product. $^1$H NMR (400 MHz, DMSO-d$_6$) δ ppm 0.56 (ddd, J=6.67, 4.45, 4.22 Hz, 2 H) 0.72 (td, J=6.98, 5.06 Hz, 2 H) 2.82 (ddd, J=7.44, 3.61, 3.38 Hz, 1 H) 7.53-7.59 (m, 1 H) 7.89-7.97 (m, 1 H) 8.10 (d, J=7.98 Hz, 1 H) 8.19 (dd, J=7.98, 1.23 Hz, 1 H) 8.26 (s, 1 H) 8.34 (d, J=3.38 Hz, 1 H) 10.69 (s, 1 H).

EXAMPLE 74

5-Oxo-4,5-dihydropyrazolo[1,5-a]quinazoline-3-carboxamide

The title compound was prepared as described in Example 69B, substituting ammonia for 1-methyl piperazine in Example 69B. The mixture was evaporated and purified by chromatography on silica gel with 10% MeOH/CH$_2$Cl$_2$ to provide the desired product. $^1$H H NMR (400 MHz, DMSO-d$_6$) δ ppm 7.32 (s, 1 H) 7.54-7.63 (m, 1 H) 7.84 (s, 1 H) 7.90-7.97 (m, 1 H) 8.11 (d, J=8.29 Hz, 1 H) 8.19 (dd, J=7.98, 1.23 Hz, 1 H) 8.29 (s, 1 H) 10.62 (s, 1 H)

EXAMPLE 75

N-Methyl-5-Oxo-4,5-dihydropyrazolo[1,5-a]quinazoline-3-carboxamide

The title compound was prepared as described in Example 69B, substituting methanamine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 2.78 (d, J=4.58 Hz, 3 H) 7.57 (t, J=7.63 Hz, 1 H) 7.91-7.96 (m, 1 H) 8.10 (d, J=8.24 Hz, 1 H) 8.18 (d, J=7.63 Hz, 1 H) 8.26 (s, 1 H) 8.31 (d, J=4.58 Hz, 1 H) 10.70 (s, 1 H).

EXAMPLE 76

N-Ethyl-5-oxo-4,5-dihydropyrazolo[1,5-a]quinazoline-3-carboxamide

The title compound was prepared as described in Example 69B, substituting ethanamine for 1-methyl piperazine in Example 69B. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 1.14 (t, J=7.17 Hz, 3 H) 3.23-3.30 (m, 2 H) 7.54-7.60 (m, 1 H) 7.91-7.97 (m, 1 H) 8.09-8.14 (m, 2 H) 8.19 (dd, J=7.48, 2.59 Hz, 1 H) 8.29-8.36 (m, 1 H).

EXAMPLE 77

N-Benzyl-5-oxo-4,5-dihydropyrazolo[1,5-a]quinazoline-3-carboxamide

The title compound was prepared as described in Example 69B, substituting phenylmethanamine for 1-methyl piperazine in Example 69B. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 4.49 (d, J=5.80 Hz, 2 H) 7.23-7.31 (m, 1 H) 7.35 (d, J=4.27 Hz, 4 H) 7.57 (t, J=7.17 Hz, 1 H) 7.91-7.97 (m, 1 H) 8.11 (d, J=7.63 Hz, 1 H) 8.19 (dd, J=7.93, 1.22 Hz, 1 H) 8.36 (s, 1 H) 8.90 (t, J=5.95 Hz, 1 H) 10.74 (s, 1 H).

EXAMPLE 78

5-Oxo-N-(2-phenylethyl)-4,5-dihydropyrazolo[1,5-a]quinazoline-3-carboxamide

The title compound was prepared as described in Example 69B, substituting phenethylamine for 1-methyl piperazine in Example 69B. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 2.82-2.89 (m, 2 H) 3.45-3.51 (m, 2 H) 7.21 (t, J=7.17 Hz, 1 H) 7.25-7.33 (m, 4 H) 7.57 (t, J=7.63 Hz, 1 H) 7.91-7.97 (m, 1 H) 8.10 (d, J=7.93 Hz, 1 H) 8.18 (dd, J=7.93, 1.22 Hz, 1 H) 8.30 (s, 1 H) 8.48 (t, J=5.49 Hz, 1 H).

EXAMPLE 79

3-(Azepane-1-carbonyl)pyrazolo[1,5-a]quinazolin-5(4H)-one

The title compound was prepared as described in Example 69B, substituting azepane for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 1.51-1.57 (m, 4 H) 1.75 (s, 4 H) 3.57 (s, 2 H) 3.70 (s, 2 H) 7.57 (t, J=7.63 Hz, 1 H) 7.92-7.97 (m, 1 H) 8.09-8.15 (m, 2 H) 8.18-8.20 (m, 1 H) 11.29 (s, 1 H).

EXAMPLE 80

3-(Morpholine-4-carbonyl)pyrazolo[1,5-a]quinazolin-5(4H)-one

The title compound was prepared as described in Example 69B, substituting morpholine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 3.34 (s, 8 H) 7.54-7.58 (m, 1 H) 7.91-7.95 (m, 1 H) 8.08-8.13 (m, 2 H) 8.16-8.19 (m, 1 H).

EXAMPLE 81

3-(piperazin-1-ylcarbonyl)pyrazolo[1,5-a]quinazolin-5(4H)-one

The title compound was prepared as described in Example 69B, substituting tert-butyl piperazine-1-carboxylate for 1-methyl piperazine in Example 69B. The reaction mix was evaporated then treated with 1 mL CH$_2$Cl$_2$ and 1 mL of TFA and stirred for 1 hr then evaporated. The mixture was evaporated and purified by chromatography on silica gel with 10% MeOH/CH$_2$Cl$_2$/0.1% NH$_4$OH to provide the desired product. $^1$H NMR (500 MHz, DMSO-d$_6$) δ ppm 2.84-2.90 (m, 4 H) 3.60-3.66 (m, 4 H) 7.54 (t, J=7.48 Hz, 1 H) 7.89-7.94 (m, 1 H) 8.05 (s, 1 H) 8.11 (d, J=8.24 Hz, 1 H) 8.17 (d, J=7.93 Hz, 1 H).

EXAMPLE 82

N-Cyclohexyl-5-oxo-4,5-dihydropyrazolo[1,5-a]quinazoline-3-carboxamide

The title compound was prepared as described in Example 69B, substituting cyclohexylamine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 1.11-1.19 (m, 1 H) 1.25-1.34 (m, 4 H) 1.62 (d, J=12.82 Hz, 1 H) 1.71-1.78 (m, 2 H) 1.85 (d, J=8.85 Hz, 2 H) 3.77 (dd, J=7.48, 3.81 Hz, 1 H) 7.56 (t, J=7.63 Hz, 1 H) 7.91-7.96 (m, 1 H) 8.11 (t, J=8.24 Hz, 2 H) 8.18 (d, J=7.93 Hz, 1 H).

EXAMPLE 83

3-(1H-Imidazol-1-ylcarbonyl)pyrazolo[1,5-a]quinazolin-5(4H)-one

The title compound was prepared as described in Example 69B, substituting pyridin-4-amine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 7.18 (s, 1 H) 7.63 (t, J=7.63 Hz, 1 H) 7.85 (s, 1 H) 7.96-8.02 (m, 1 H) 8.20 (dd, J=19.68, 7.48 Hz, 2 H) 8.45-8.50 (m, 2 H).

EXAMPLE 84

5-Oxo-N-(piperidin-4-ylmethyl-4,5-dihydropyrazolo[1,5-a]quinazoline-3-carboxamide The title compound was prepared as described in Example 69, substituting tert-butyl 4-(aminomethyl)piperidine-1-carboxylate for 1-methyl piperazine in Example 69B. The reaction mix was evaporated then treated with 1 mL CH$_2$Cl$_2$ and 1 mL of TFA and stirred for 1 hr then evaporated. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 1.34 (d, J=12.21 Hz, 2 H) 1.82 (s, 3 H) 2.87 (s, 2 H) 3.16-3.21 (m, 3 H) 7.58 (t, J=7.63 Hz, 1 H) 7.93-7.97 (m, 1 H) 8.11 (d, J=7.63 Hz, 1 H) 8.19 (dd, J=7.93, 1.22 Hz, 1 H) 8.45 (t, J=5.80 Hz, 2 H).

EXAMPLE 85

3-(3-(Aminomethyl)piperidine-1-carbonyl)pyrazolo[1,5-a]quinazolin-5(4H)-one

The title compound was prepared as described in Example 69B, substituting tert-butyl piperidin-3-ylmethylcarbamate for 1-methyl piperazine in Example 69B. The reaction mix was evaporated then treated with 1 mL CH$_2$Cl$_2$ and 1 mL of TFA and stirred for 1 hr then evaporated. The residue was purified by HPLC on a C18 column with 0-100% CH$_3$CN/H$_2$O/0.1% TFA to provide the desired product as the trifluoroacetate salt. $^1$H NMR (400 MHz, DMSO-d$_6$) δ ppm 1.26-1.36 (m, 1 H) 1.39-1.50 (m, 1 H) 1.66-1.75 (m, 1 H) 1.80-1.91 (m, 2 H) 2.78 (qd, J=12.79, 7.06 Hz, 2 H) 2.93 (s, 1 H) 3.38-3.41 (m, 1 H) 4.14 (s, 2 H) 7.53-7.62 (m, 1 H) 7.91-7.97 (m, 1 H) 8.06 (s, 1 H) 8.10-8.21 (m, 2 H).

EXAMPLE 86

5-Oxo-N-phenyl-4,5-dihydropyrazolo[1,5-a]quinazoline-3-carboxamide

The title compound was prepared as described in Example 69B, substituting aniline for 1-methyl piperazine in Example 69B. The mixture was evaporated and purified by chromatography on silica gel with 10% MeOH/CH$_2$Cl$_2$ to provide the desired product. $^1$H NMR (400 MHz, DMSO-d$_6$) δ ppm 7.11 (t, J=7.36 Hz, 1 H) 7.37 (t, J=7.98 Hz, 2 H) 7.59 (t, J=7.67 Hz, 1 H) 7.73 (d, J=7.67 Hz, 2 H) 7.93-7.99 (m, 1 H) 8.13-8.23 (m, 2 H) 8.53 (s, 1 H) 10.05 (s, 1 H) 10.93 (s, 1 H).

EXAMPLE 87

4-{[(5-Oxo-4,5-dihydropyrazolo[1,5-a]quinazolin-3-yl)carbonyl]amino}butanoic acid The title compound was prepared as described in Example 69B, substituting 4-aminobutanoic acid for 1-methyl piperazine in Example 69B. The mixture was evaporated and purified by chromatography on silica gel with 10% MeOH/CH$_2$Cl$_2$ to provide the desired product. $^1$H NMR (400 MHz, DMSO-d$_6$) δ ppm 1.76 (dq, J=7.36, 7.16 Hz, 2 H) 2.30 (t, J=7.36 Hz, 2 H) 3.25-3.30 (m, 2 H) 7.56 (t, J=7.67 Hz, 1 H) 7.89-7.96 (m, 1 H) 8.10 (d, J=7.67 Hz, 1 H) 8.18 (dd, J=7.98, 1.23 Hz, 1 H) 8.29 (s, 1 H) 8.34-8.38 (m, 1 H).

EXAMPLE 88

3-(5-Oxo-4,5-dihydropyrazolo[1,5-a]quinazolin-2-yl)methyl)benzoic acid

Example 68 (0.15 g, 0.45 mmol) was dissolved in EtOH (10 mL), treated with a 1M solution of sodium hydroxide (3 mL, 3 mmol) and the mixture was heated at 80° C. for 18 hr. The mixture was filtered then acidified with acetic acid and 10% HCl. The precipitated product was filtered, washed with H$_2$O and Et$_2$O then dried well. $^1$H NMR (500 MHz, DMSO-d$_6$) δ ppm 4.04-4.11 (m, 2 H) 5.71 (s, 1 H) 7.45 (td, J=7.63, 4.58 Hz, 2 H) 7.59 (d, J=8.24 Hz, 1 H) 7.80 (d, J=7.63 Hz, 1 H) 7.84-7.90 (m, 2 H) 8.04 (d, J=8.24 Hz, 1 H) 8.12 (d, J=7.02 Hz, 1 H) 12.11 (s, 1 H) 12.93 (s, 1 H).

EXAMPLE 89

5-Oxo-N-(2-(piperidin-1-yl)ethyl)-4,5-dihydropyrazolo[1,5-a]quinazoline-3-carboxamide The title compound was prepared as described in Example 69B, substituting 2-(piperidin-1-yl)ethanamine for 1-methyl piperazine in Example 69B. The mixture was evaporated and purified by chromatography on silica gel with 10% MeOH/CH$_2$Cl$_2$ to provide the desired product. $^1$H NMR (500 MHz, DMSO-d$_6$) δ ppm 1.39-1.41 (m, 1 H) 1.64-1.73 (m, 3 H) 1.84 (d, J=14.34 Hz, 2 H) 2.92-3.00 (m, 2 H) 3.24 (q, J=5.80 Hz, 2 H) 3.56 (d, J=11.60 Hz, 2 H) 3.63 (q, J=6.10 Hz, 2 H) 7.59 (t, J=7.63 Hz, 1 H) 7.93-7.99 (m, 1 H) 8.12 (d, J=7.93 Hz, 1 H) 8.20 (dd, J=7.93, 1.22 Hz, 1 H) 8.29 (s, 1 H) 8.68 (t, J=5.65 Hz, 1 H) 10.81 (s, 1 H).

EXAMPLE 90

3-(Hydroxymethyl)pyrazolo[1,5-a]quinazolin-5-(4H)-one

EXAMPLE 90A

Methyl-5-oxo-4,5-dihydropyrazolo[1,5-a]quinazoline-3-carboxylate

A mixture of 2-hydrazinylbenzoic acid hydrochloride (1.05 g, 5.57 mmol), (E)-ethyl 2-cyano-3-ethoxyacrylate (0.9 g, 5.32 mmol) and sodium acetate (0.457 g, 5.57 mmol) in DMF (7 mL) was heated to 140° C. for 2 h then cooled. Water (5 mL) was added and the mixture was stirred at ambient temperature for 1 h then filtered. The solid was washed with H$_2$O, EtOH and Et$_2$O then dried.

EXAMPLE 90B 3-(Hydroxymethyl)pyrazolo[1,5-a]quinazolin-5-(4H)-one

A mixture Example 90A (0.1 g, 0.39 mmol) and lithium aluminum hydride (0.044 g, 1.16 mmol) in THF (5 mL) was refluxed for 3 h then cooled and quenched with water and 15% NaOH. The mixture was filtered, evaporated and purified by chromatography on silica gel with 10% MeOH/CH$_2$Cl$_2$ to provide the desired product. $^1$H NMR (500 MHz, DMSO-d$_6$) δ ppm 4.47 (s, 2 H) 7.46-7.52 (m, 1 H) 7.78 (s, 1 H) 7.83-7.91 (m, 1 H) 8.07 (d, J=7.93 Hz, 1 H) 8.14 (dd, J=7.93, 1.22 Hz, 1 H) 12.15 (s, 1 H).

EXAMPLE 91

3-(5-Oxo-4,5-dihydro pyrazolo[1,5-a]quinazolin-2-yl)methyl)benzamide

A mixture Example 88 (0.15 g, 0.47 mmol), 2M solution of NH$_3$ in MeOH (0.5 mL, 0.1 mmol) and CDI (0.076 g, 0.54 mmol) in DMF (1 mL) and pyridine (1 mL) was stirred overnight at ambient temperature then evaporated. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 4.04 (s, 2 H) 5.69 (s, 1 H) 7.33 (s, 1 H) 7.39 (t, J=7.63 Hz, 1 H) 7.44-7.49 (m, 2 H) 7.73 (d, J=7.63 Hz, 1 H) 7.81-7.89 (m, 2 H) 7.95 (s, 1 H) 8.04 (d, J=7.93 Hz, 1 H) 8.11 (dd, J=7.93, 1.22 Hz, 1 H) 12.11 (s, 1 H).

EXAMPLE 92

3-(Aminomethyl)pyrazolo[1,5-a]quinazolin-5-(4H)-one

EXAMPLE 92A

Methyl-5-oxo-4,5-dihydropyrazolo[1,5-a]quinazoline-3-carboxylate

A mixture of 2-hydrazinylbenzoic acid hydrochloride (10 g, 53 mmol), 2-(ethoxymethylene)malononitrile (6.5 g, 53.2 mmol) and sodium ethoxide (4.85 g, 257 mmol) in EtOH (100 mL) was refluxed overnight then cooled to ambient temperature. Water was added and the mixture was stirred at ambient temperature for 1 h then filtered. The solid was washed with H$_2$O, EtOH and Et$_2$O then dried.

EXAMPLE 92B 3-(Aminomethyl)pyrazolo[1,5-a]quinazolin-5-(4H)-one

The title compound was prepared as described in Example 63. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 4.08 (s, 2 H) 7.54 (t, J=7.63 Hz, 1 H) 7.89 (s, 1 H) 7.90-7.94 (m, 1 H) 8.00 (s, 1 H) 8.11 (d, J=7.93 Hz, 1 H) 8.18 (dd, J=7.93, 1.22 Hz, 1 H).

EXAMPLE 93

N-[(5-Oxo-4,5-dihydropyrazolo[1,5-a]quinazolin-3-yl)methyl]glycine

A mixture of Example 92B (0.1 g, 0.47 mmol), 2-oxoacetic acid (0.035 g, 0.47 mmol) and sodium cyanoborohydride (0.029 g, 0.45 mmol) in MeOH (2 mL) was refluxed overnight then evaporated. The residue was purified by HPLC on a C18 column with 0-100% CH$_3$CN/H$_2$O/0.1% TFA to provide the desired product as the trifluoroacetate salt. $^1$H NMR (400 MHz, DMSO-d$_6$) δ ppm 2.54 (s, 2 H) 4.08 (q, J=5.42 Hz, 2 H) 7.52-7.57 (m, 1 H) 7.89-8.00 (m, 4 H) 8.11 (d, J=7.67 Hz, 1 H) 8.18 (d, J=7.06 Hz, 1 H) 12.34 (s, 1 H).

EXAMPLE 94

4-Chloro-N-((5-Oxo-4,5-dihydropyrazolo[1,5-a]quinazolin-3-yl)methyl)butanamide

A mixture of Example 92B (0.1 g, 0.47 mmol), 4-chlorobutanoyl chloride (0.066 g, 0.47 mmol) in DMF (1 mL) and pyridine (1 mL) was stirred overnight at room temperature then evaporated. The residue was purified by HPLC on a C18 column with 0-100% CH$_3$CN/H$_2$O/0.1% TFA to provide the desired product as the trifluoroacetate salt. $^1$H NMR (400 MHz, DMSO-d$_6$) δ ppm 1.92-2.00 (m, J=6.98, 6.98, 6.98, 6.98 Hz, 2 H) 2.27 (t, J=7.36 Hz, 2 H) 3.63 (q, J=6.55 Hz, 2 H) 4.21 (d, J=5.52 Hz, 2 H) 7.47-7.53 (m, 1 H) 7.86-7.92 (m, 1 H) 8.07 (d, J=7.98 Hz, 1 H) 8.15 (dd, J=7.98, 1.23 Hz, 1 H) 11.96 (s, 1 H).

EXAMPLE 95

4-Oxo-4-((5-oxo-4,5-dihydropyrazolo[1,5-a]quinazolin-3-yl)methylamino)butanoic acid A mixture of Example 92B (0.1 g, 0.47 mmol) and dihydrofuran-2,5-dione (0.047 g, 0.47 mmol) in CH$_3$CN (2 mL) was heated to 80° C. overnight then evaporated. The residue was purified by HPLC on a C18 column with 0-100% CH$_3$CN/H$_2$O/0.1% TFA to provide the desired product as the trifluoroacetate salt. $^1$H NMR (500 MHz, DMSO-d$_6$) δ ppm 2.35 (t, J=7.02 Hz, 2 H) 2.46 (t, J=6.71 Hz, 2 H) 4.20 (d, J=5.49 Hz, 2 H) 7.49 (t, J=7.63 Hz, 1 H) 7.69-7.73 (m, 1 H) 7.85-7.91 (m, 1 H) 8.06 (d, J=7.63 Hz, 1 H) 8.10-8.17 (m, 1 H) 8.27 (t, J=5.49 Hz, 1 H) 12.01 (s, 1 H).

EXAMPLE 96

1-Acetyl-N-((5-oxo-4,5-dihydropyrazolo[1,5-a]quinazolin-3-yl)methyl)piperidine-4-carboxamide A mixture of Example 92B (0.1 g, 0.47 mmol) and 1-acetylpiperidine-4-carbonyl chloride (0.089 g, 0.47 mmol) in DMF (1 mL) and pyridine (1 mL) was stirred overnight. The precipitated solids were filtered and washed with $H_2O$ and $Et_2O$ then dried well. $^1$H NMR (500 MHz, DMSO-$d_6$) δ ppm 1.32-1.41 (m, 1 H) 1.46-1.55 (m, 1 H) 1.69 (t, J=14.19 Hz, 2 H) 1.98 (s, 3 H) 2.35-2.41 (m, 1 H) 2.52-2.60 (m, 1 H) 3.00 (dd, J=12.21, 10.68 Hz, 1 H) 3.80 (d, J=13.73 Hz, 1 H) 4.20 (d, J=5.80 Hz, 2 H) 4.33 (d, J=13.43 Hz, 1 H) 7.47-7.52 (m, 1 H) 7.70 (s, 1 H) 7.86-7.92 (m, 1 H) 8.06 (d, J=8.24 Hz, 1 H) 8.15 (dd, J=7.93, 1.22 Hz, 1 H) 8.24 (t, J=5.49 Hz, 1 H) 11.97 (s, 1 H).

EXAMPLE 97

2-oxo-2-{[(5-oxo-4,5-dihydropyrazolo[1,5-a]quinazolin-3-yl)methyl]amino}ethyl acetate The title compound was prepared as described in Example 96, substituting 2-chloro-2-oxoethyl acetate for 1-acetylpiperidine-4-carbonyl chloride. $^1$H NMR (400 MHz, DMSO-$d_6$) δ ppm 2.09 (s, 3 H) 4.25 (d, J=5.83 Hz, 2 H) 4.47 (s, 2 H) 7.47-7.52 (m, 1 H) 7.70 (s, 1 H) 7.85-7.91 (m, 1 H) 8.07 (d, J=8.29 Hz, 1 H) 8.15 (d, J=7.98 Hz, 1 H) 8.36 (t, J=5.52 Hz, 1 H)

EXAMPLE 98

3-(Pyrrolidin-1-ylmethyl)pyrazolo[1,5-a]quinazolin-5-(4H)-one

A mixture of Example 92B (0.1 g, 0.47 mmol), 1-bromo-4-chlorobutane (0.08 g, 0.47 mmol) and sodium ethoxide (0.032 g, 0.47 mmol) in EtOH (2 mL) was stirred overnight then evaporated. The residue was purified by HPLC on a C18 column with 0-100% $CH_3CN/H_2O$/0.1% TFA to provide the desired product as the trifluoroacetate salt. $^1$H NMR (500 MHz, DMSO-$d_6$) δ ppm 1.84 (ddd, J=6.87, 3.66, 3.51 Hz, 3 H) 3.08-3.10 (m, 5 H) 4.09 (s, 2 H) 7.54 (t, J=7.63 Hz, 1 H) 7.90-7.99 (m, 2 H) 8.11 (d, J=8.54 Hz, 1 H) 8.18 (d, J=7.93 Hz, 1 H)

EXAMPLE 99

1-((5-Oxo-4,5-dihydropyrazolo[1,5-a]quinazolin-3-yl)methyl)pyrrolidine-2,5-dione A mixture Example 95 (0.05 g, 0.44 mmol) and CDI (0.039 g, 0.24 mmol) in DMF (2 mL) was stirred overnight at ambient temperature. The mixture was evaporated and purified by chromatography on silica gel with 10% $MeOH/CH_2Cl_2$ to provide the desired product. $^1$H NMR (500 MHz, DMSO-$d_6$) δ ppm 2.66 (s, 4 H) 4.59 (s, 2 H) 7.47-7.54 (m, 1 H) 7.62 (s, 1 H) 7.88 (s, 1 H) 8.05 (d, J=8.24 Hz, 1 H) 8.16 (d, J=7.02 Hz, 1 H)

EXAMPLE 100

N-((5-Oxo-4,5-dihydropyrazolo[1,5-a]quinazolin-3-yl)methyl)acetamide

A mixture of Example 92B (0.1 g, 0.47 mmol), acetic anhydride (0.048 g, 0.47 mmol) and diisopropyl ethylamine (0.2 ml, 1.15 mmol) in MeOH (2 ml) was heated to 40° C. overnight. The mixture was evaporated and purified by chromatography on silica gel with 10% $MeOH/CH_2Cl_2$ to provide the desired product. $^1$H NMR (500 MHz, DMSO-$d_6$) δ ppm 1.85 (s, 3 H) 4.19 (d, J=5.49 Hz, 2 H) 7.49 (t, J=7.48 Hz, 1 H) 7.73 (s, 1 H) 7.88 (t, J=7.48 Hz, 1 H) 8.06 (d, J=8.24 Hz, 1 H) 8.15 (d, J=7.63 Hz, 1 H) 8.26 (s, 1 H)

What is claimed is:
1. A compound of Formula (I)

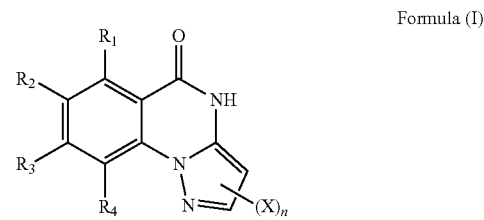

Formula (I)

or a pharmaceutically acceptable salt thereof, wherein
$R_1$, $R_2$, $R_3$ and $R_4$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

X is heterocyclealkyl, wherein X is unsubstituted or substituted with 1, 2, 3, 4, or 5 substituents, Z, independently selected from the group consisting of alkyl, alkenyl, alkynyl, nitro, —CN, halogen, haloalkyl, alkoxy, alkylcarbonyl, alkylcarbonylalkyl, alkoxyalkyl, alkoxycarbonyl, alkoxycarbonylalkyl, aryl, arylalkyl, arylalkoxy, arylalkoxycarbonyl, arylalkylcarbonyl, carboxy, carboxyalkyl, cycloalkyl, cycloalkylalkyl, cycloalkylalkoxy, cycloalkylcarbonyl, heteroaryl, heteroarylalkyl, heteroarylcarbonyl, heteroarylcarbonylalkyl, heterocycle, heterocyclealkyl, heterocyclealkylcarbonyl, heterocyclecarbonyl, heterocyclecarbonylalkyl, hydroxy, hydroxyalkyl, $NR_CR_D$, $(NR_CR_D)$alkyl, $(NR_CR_D)$carbonyl, $(NR_CR_D)$carbonylalkyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;

$R_C$ and $R_D$ are independently selected from the group consisting of hydrogen, alkyl, alkylcarbonyl, alkylcarbonyloxyalkylcarbonyl, arylcarbonyl, aryl, arylalkyl, arylalkylcarbonyl, carboxyalkyl, carboxyalkylcarbonyl, cycloalkyl, cycloalkylalkyl, haloalkyl, haloalkylcarbonyl, heteroaryl, heteroarylalkyl, heteroarylcarbonyl, heterocycle, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are aryl, arylalkyl, arylalkylcarbonyl, arylcarbonyl, cycloalkyl, cycloalkylalkyl, heteroaryl, heteroarylalkyl, heteroarylcarbonyl, heterocycle, heterocyclealkyl, heterocyclecarbonyl, or heterocyclealkylcarbonyl, then $R_C$ or $R_D$ may be unsubstituted or substituted with 1, 2, 3, 4, or 5 substituents independently selected from the group consisting of alkyl, alkenyl, alkynyl, nitro, —CN, halogen, haloalkyl, oxo, alkoxy, alkylcarbonyl, alkylcarbonylalkyl, alkoxyalkyl, alkoxycarbonyl, alkoxycarbonylalkyl, aryl, arylalkyl, arylalkoxy, arylalkylcarbonyl, and arylalkoxycarbonyl;

$R_A$ and $R_B$ are independently selected from the group consisting of hydrogen, alkyl, haloalkyl, and alkylcarbonyl; and n is 1.

2. The compound of claim 1 having Formula (II):

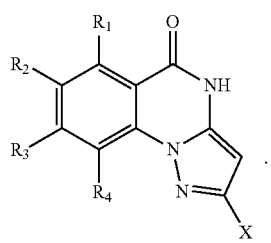

Formula (II)

3. The compound of claim 2, wherein
X is heterocyclealkyl, wherein X is unsubstituted or substituted with 1 or 2 substituents, Z, independently selected from the group consisting of alkyl, nitro, —CN, halogen, alkoxy, alkoxycarbonyl, aryl, arylalkyl, arylalkoxycarbonyl, carboxy, cycloalkylalkyl, heteroaryl, heteroarylalkyl, heterocycle, heterocyclealkyl, heterocyclealkylcarbonyl, $NR_CR_D$, $(NR_CR_D)$alkyl, $(NR_CR_D)$carbonyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;
$R_C$ and $R_D$ are independently selected from the group consisting of hydrogen, alkyl, alkylcarbonyl, alkylcarbonyloxyalkylcarbonyl, aryl, arylalkyl, arylalkylcarbonyl, arylcarbonyl, carboxyalkyl, carboxyalkylcarbonyl, cycloalkyl, haloalkyl, haloalkylcarbonyl, heteroaryl, heteroarylcarbonyl, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are arylalkylcarbonyl, arylcarbonyl, heteroarylcarbonyl, heterocyclealkyl, heterocyclecarbonyl, or heterocyclealkylcarbonyl, then $R_C$ or $R_D$ may be unsubstituted or substituted with one substituent selected from the group consisting of alkoxy, alkylcarbonyl and arylalkoxycarbonyl; and
$R_A$ and $R_B$ are independently selected from the group consisting of hydrogen, alkyl, and alkylcarbonyl.

4. The compound of claim 3, wherein $R_1$, $R_2$, $R_3$ and $R_4$ are hydrogen.

5. The compound of claim 1 having Formula (III):

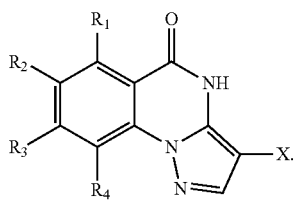

Formula (III)

6. The compound of claim 5, wherein
X is heterocyclealkyl, wherein X is unsubstituted or substituted with 1 or 2 substituents, Z, independently selected from the group consisting of alkyl, nitro, —CN, halogen, alkoxy, alkoxycarbonyl, aryl, arylalkyl, arylalkoxycarbonyl, carboxy, cycloalkylalkyl, heteroaryl, heteroarylalkyl, heterocycle, heterocyclealkyl, heterocyclealkylcarbonyl, $NR_CR_D$, $(NR_CR_D)$alkyl, $(NR_CR_D)$carbonyl, and oxo; wherein the aryl and the heteroaryl moieties of Z are independently unsubstituted or substituted with 1, 2, 3, 4, or 5 substituents selected from the group consisting of alkyl, formyl, halogen, and haloalkyl, and the heterocycle and cycloalkyl moieties of Z are independently unsubstituted or substituted with 1, 2, 3, 4, or 5 substituents selected from the group consisting of alkyl, oxo, formyl, halogen, and haloalkyl;
$R_C$ and $R_D$ are independently selected from the group consisting of hydrogen, alkyl, alkylcarbonyl, alkylcarbonyloxyalkylcarbonyl, aryl, arylalkyl, arylalkylcarbonyl, arylcarbonyl, carboxyalkyl, carboxyalkylcarbonyl, cycloalkyl, haloalkyl, haloalkylcarbonyl, heteroaryl, heteroarylcarbonyl, heterocyclealkyl, heterocyclecarbonyl, heterocyclealkylcarbonyl, $(NR_AR_B)$alkyl, and $(NR_AR_B)$alkylcarbonyl; wherein if $R_C$ or $R_D$ are arylalkylcarbonyl, arylcarbonyl, heteroarylcarbonyl, heterocyclealkyl, heterocyclecarbonyl, or heterocyclealkylcarbonyl, then $R_C$ or $R_D$ may be unsubstituted or substituted with one substituent selected from the group consisting of alkoxy, alkylcarbonyl and arylalkoxycarbonyl; and
$R_A$ and $R_B$ are independently selected from the group consisting of hydrogen, alkyl, and alkylcarbonyl.

7. The compound of claim 6, wherein $R_1$, $R_2$, $R_3$ and $R_4$ are hydrogen.

8. The compound of claim 1, selected from the group consisting of
2-piperidin-3-yl-4H-pyrazolo[1,5-a]quinazolin-5-one;
2-(1-methylpiperidin-3-yl)-4H-pyrazolo[1,5-a]quinazolin-5-one;
2-(1-ethylpiperidin-3-yl)-4H-pyrazolo[1,5-a]quinazolin-5-one;
2-(1-isobutylpiperidin-3-yl)-4H-pyrazolo[1,5-a]quinazolin-5-one;
2-(1-cyclopropylmethylpiperidin-3-yl)-4H-pyrazolo[1,5-a]quinazolin-5-one;
2-[1-(3-piperidin-1-ylpropionyl)piperidin-3-yl]-4H-pyrazolo[1,5-a]quinazolin-5-one;
2-(1-propylpiperidin-3-yl)-4H-pyrazolo[1,5-a]quinazolin-5-one;
2-(1-benzylpiperidin-3-yl)-4H-pyrazolo[1,5-a]quinazolin-5-one;
2-(1-cyclopentylmethylpiperidin-3-yl)-4H-pyrazolo[1,5-a]quinazolin-5-one;
2-(1-pyridin-4-ylmethylpiperidin-3-yl)-4H-pyrazolo[1,5-a]quinazolin-5-one;
2-(1-isopropylpiperidin-3-yl)-4H-pyrazolo[1,5-a]quinazolin-5-one;
2-(1-benzylpiperidin-4-yl)-4H-pyrazolo[1,5-a]quinazolin-5-one;
2-piperidin-4-yl-4H-pyrazolo[1,5-a]quinazolin-5-one;
2-(1-methylpiperidin-4-yl)-4H-pyrazolo[1,5-a]quinazolin-5-one;
2-(1-ethylpiperidin-4-yl)-4H-pyrazolo[1,5-a]quinazolin-5-one;
2-(1-propylpiperidin-4-yl)-4H-pyrazolo[1,5-a]quinazolin-5-one;
2-(1-cyclopropylmethylpiperidin-4-yl)-4H-pyrazolo[1,5-a]quinazolin-5-one;
2-(1-isobutylpiperidin-4-yl)-4H-pyrazolo[1,5-a]quinazolin-5-one;

2-(1-isopropylpiperidin-4-yl-4H-pyrazolo[1,5-a]quinazolin-5-one;
2-pyrrolidin-3-yl-4H-pyrazolo[1,5-a]quinazolin-5-one;
benzyl 3-(5-oxo-4,5-dihydropyrazolo[1,5-a]quinazolin-2-yl)pyrrolidine-1-carboxylate;
2-(1-methylpyrrolidin-3-yl)-4H-pyrazolo[1,5-a]quinazolin-5-one;
2-(1-ethylpyrrolidin-3-yl)-4H-pyrazolo[1,5-a]quinazolin-5-one;
2-(1-cyclopropylmethylpyrrolidin-3-yl)-4H-pyrazolo[1,5-a]quinazolin-5-one;
2-piperidin-2-yl-4H-pyrazolo[1,5-a]quinazolin-5-one; and
2-(1-methylpiperidin-2-yl)-4H-pyrazolo[1,5-a]quinazolin-5-one;

or a pharmaceutically acceptable salt thereof

9. A pharmaceutical composition comprising a compound of Formula (I) of claim 1 or a pharmaceutically acceptable salt thereof, in combination with a therapeutically acceptable carrier.

* * * * *